United States Patent [19]

Markland et al.

[11] Patent Number: 5,795,865
[45] Date of Patent: Aug. 18, 1998

[54] KALLIKREIN-INHIBITING "KUNITZ DOMAIN" PROTEINS AND ANALOGUES THEREOF

[75] Inventors: Willaim Markland, Milford, Mass.; Robert Charles Ladner, Ijamsville, Md.

[73] Assignee: Dyax Corp., Cambridge, Mass.

[21] Appl. No.: 676,125

[22] PCT Filed: Jan. 11, 1995

[86] PCT No.: PCT/US95/00299

§ 371 Date: Sep. 25, 1996

§ 102(e) Date: Sep. 25, 1996

[87] PCT Pub. No.: WO95/21601

PCT Pub. Date: Aug. 17, 1995

Related U.S. Application Data

[63] Continuation-in-part of Ser. No. 208,264, Mar. 10, 1994, abandoned, and a continuation-in-part of Ser. No. 179,964, Jan. 11, 1994, abandoned.

[51] Int. Cl.$^6$ ............. A61K 38/12; C07K 5/12; C07K 1/22; G01N 33/53
[52] U.S. Cl. ............. 514/12; 435/7.1; 435/7.6; 435/7.71; 435/7.72; 530/317; 530/412
[58] Field of Search ............ 530/317, 412; 514/12; 435/4, 7.1, 7.6, 7.71, 7.72

[56] References Cited

U.S. PATENT DOCUMENTS

| | | | |
|---|---|---|---|
| 3,691,016 | 9/1972 | Patel | 435/181 |
| 3,969,287 | 7/1976 | Jaworek et al. | 526/238.1 |
| 4,118,481 | 10/1978 | Schnabel et al. | 514/12 |
| 4,153,687 | 5/1979 | Schnabel et al. | 514/12 |
| 4,179,337 | 12/1979 | Davis et al. | 435/181 |
| 4,195,128 | 3/1980 | Hildebrand et al. | 435/178 |
| 4,229,537 | 10/1980 | Hodgins et al. | 435/177 |
| 4,247,642 | 1/1981 | Hirohara et al. | 435/181 |
| 4,330,440 | 5/1982 | Ayers et al. | 525/54.31 |
| 4,609,725 | 9/1986 | Brady et al. | 530/324 |
| 5,223,409 | 6/1993 | Ladner et al. | 435/69.7 |

FOREIGN PATENT DOCUMENTS

| | | |
|---|---|---|
| 0 285 123 A2 | 10/1988 | European Pat. Off. |
| 93/14120 | 7/1993 | WIPO |
| 93/14121 | 7/1993 | WIPO |
| 93/14122 | 7/1993 | WIPO |
| WO-A-93 14120 | 7/1993 | WIPO |
| WO-A-93 14121 | 7/1993 | WIPO |
| WO-A-93 14122 | 7/1993 | WIPO |

OTHER PUBLICATIONS

Girard et al. Nature 338: 518–520 'Functional Synthesis of the Kunitz Type Inhibtory Domains.', Apr. 6, 1989.
Adelman et al., Blood, 68(6):1280–1284 (1986).
Albrecht et al., Hoppe–Seyler's Z Physiol. Chem., 364:1697–1702 (1983).
Albrecht et al., Hoppe–Seyler's Z Physiol Chem., 364:1703–1708 (1983).
Anba et al., Biochimie, 70(6):727–733 (1988).
Angliker et al., Biochem. J., 241(3):871–875 (1987).
Atherton et al., J. Chem. Soc. Perkin Trans., 1:538–546 (1981).
Auerswald et al., Bio. Chem. Hoppe–Seyler, 369(Suppl):27–35 (1988).
Balduyck et al., Biol. Chem. Hoppe–Seyler, 366:9–14 (1985).
Baneyx & Georgiou, J. Bacteriol., 173(8):2696–2703 (1991).
Baneyx and Georgiou, J. Bacteriol., 172(1):491–494 (1990).
Berndt et al., Biochemistry, 32(17):4564–4570 (1993).
Bhoola et al., Pharmacological Reviews, 44(1):1–80 (1992).
Browne et al., GeneBank, Accession No. M74220 (1991).
Broze et al., Biochemisty, 29(33):7539–7546 (1990).
Brus et al., Pediatr. Res. 41(1):120–127 (1997).
Budavari, ed., Merck Index, eleventh ed., ISBN 911910–28–X, entries 923, 1745, 2740, 7425 (1989).
Carey and Sundberg, Advanced Organic Chemistry, Third ed., ISBN 0–306–43456–3, pp. 678–686 (1990).
Chung et al., GenBank, Accession #125184 (1995).
Coleman et al., Proc. Assoc. Am. Physicians, 109(1):10–22 (1997).
Colman et al., Hemostasis and Trombosis, Second Edition (Colman et al., eds; ISBN 0–397–50679–1) Chap. 1, pp. 3–17 (1987).
Cumming and Nimmo, Crit. Care Med., 20(8):1134–1139 (1992).
Currie et al., Tetrahedron, 49(17):3489–3500 (1993).
DeLa Cadena et al., et al., FASEB Journal, 9:446–452 (1995).
DeLa Cadena et al., et al., Transact. Assoc. Am. Physicians, 105:229–237 (1992).
Dennis et al., J. Biol. Chem., 270(43):25411–25417 (1995).
Dennis and Lazarus, J. Biological Chem., 269(35):22129–22136 (1994).
Dennis and Lazarus, J. Biological Chem., 269(35):22137–22144 (1994).
Diaz et al., Tetrahedron, 49(17):3533–3545 (1993).
DiMaio et al., FEBS Lett. 282(1):47–52 (1991).
Eigenbrot et al., Protein Engineering, 3(7):591–598 (1990).
Ellis et al., Ann. NY Acad. Sci., 667:13–31 (1992).

(List continued on next page.)

*Primary Examiner*—Nancy Degen
*Attorney, Agent, or Firm*—Leon R. Yankwich; Iver P. Cooper

[57] ABSTRACT

Proteins are disclosed that are homologous to bovine pancreatic trypsin inhibitor (BPTI) Kunitz domains, and especially proteins that are homologous to lipoprotein-associated coagulation inhibitor (LACI) Kunitz domains, which inhibit one or more plasma and/or tissue kallikreins, and uses of such proteins in therapeutic and diagnostic methods also are disclosed. In particular, Kunitz domains derived from Kunitz domains of human origin and especially to the first Kunitz domain of LACI are disclosed.

13 Claims, No Drawings

OTHER PUBLICATIONS

Fidler and Ellis, Cell, 79:185–188 (1994).
Fields and Noble, Int. J. Peptide Protein Res., 35:161–214 (1990).
Fraedrich et al., Thorac. Cardiovasc. Surg., 37(2):89–91 (1989).
Freidinger et al., J. Org. Chem. 47(1):104–109 (1982).
Gardell, Toxicol. Pathol., 21(2):190–198 (1993).
Girard et al., J. Biol. Chem., 266(8):5036–5041 (1991).
Girard et al., Nature, 338:518–20 (1989).
Hoover et al., Biochemistry, 32:10936–10943 (1993).
Hortin and Trimpe, J. Biol. Chem., 266(11):6866–6871 (1991).
Hynes et al., Biochemistry, 29:10018–10022 (1990).
Kemp and Bowen, Tetrahedron Letts. 29(40):5077–5080 (1988).
Kido et al., Biochem. & Biophys. Res. Comm., 167(2):716–721 (1990).
Kido et al., J. Biol. Chem., 263(34):18104–18107 (1988).
Kline et al., Biochem. Biophys. Res. Commun., 177(3):1049–1055 (1991).
Kurjan and Herkowwitz, Cell, 30:933–943 (1982).
Laskowski and Kato, Ann. Rev. Biochem., 49:593–626 (1980).
Leatherbarrow and Salacinski, Biochemistry, 30(44):1071710721 (1991).
Lohmann and Marshall, Refract. Corneal. Surg. 9(4):300–302 (1993).
Lucas et al., J. Biological Chem., 258(7):4249–4256 (1983).
McConnell et al., J. Med. Chem. 33(1):86–93 (1990).
MacGilchrist et al., Clin. Sci. (Colch), 87(3):329–335 (1994).
Mann and Lundblad, Hemostasis and Thrombosis, Second Edition (Colman et al., eds; ISBN 0-397-50679-1) Chap 10, pp. 148–161 (1987).
March, Advanced Organic Chemistry, Third Edition (ISBN 0-471-88841-9) pp. 396–398;1057–1060;1099–1100 (1985).
Merrifield, Science, 232:341–347 (1986).
Merrifield, J. Amer. Chem. Soc., 85:2149–2154 (1963).
Miyajima et al., Gene, 37:155–161 (1985).
Monteseirin et al., Allergol. Immunopathol. (Madr), 20(5):211–214 (1992).
Naess et al., Eur. J. Surg., 160(2):77–86 (1994).
Nagai et al., Tetrahedron., 49(17):3577–3592 (1993).
Nagai and Sato, Tetrahedron Lett., 26(5):647–650(1985).
Neuhaus et al., Lancet, 2(8668)924–925 (1989).
Novotny et aL, J. Biol. Chem., 264(31):18832–18837 (1989).
Okamoto et al., Agents Actions Suppl., 38(Pt1):198–205 (1992).
O'Reilly et al., Cell, 79:315–328 (1994).
Park and Tulinsky, Biochemistry, 25(14):3977–3982 (1986).
Putterman, Acta Chir. Scand., 155(6–7;)367 (1989).
Robbins, Hemostasis and Thrombosis, Second Edition (Colman et al., eds; ISBN 0-397-50679-1), Chap. 21, pp. 340–357 (1987).
Scatchard, Ann. N.Y. Acad. Sci., 51:660–672 (1949).
Schechter and Berger, Biochem. Biophys. Res. Commun. 32(5):898–902 (1968).
Schechter and Berger, Biochem. Biochem. Biophys. Res. Commun., 27(2):157–162 (1967).
Schmaier et al., Hemostasis and Thrombosis, Second Edition (Colman et al., eds; ISBN 0-397-50679-1), Chap.2, pp. 18–38 (1987).
Schmidt et al., Swiss-Prot, Accession #124392 (1992).
Schnabel et al., Biol. Chem. Hoppe-Seyler, 367:1167–1176 (1986).
Sheppard and Williams, Int. J. Peptide Protein Res., 20:451–454 (1982).
Sheridan et al., Dis. Colon Rectum, 32(6):505–508 (1989.
Sprecher et al., PNAS USA, 91:3353–3357 (1994).
Stadnicki et al., J. Invest. Med., 44(3):299A (1996).
Stadnicki et al., 10th World Cong. Gastroenterology, Poster #1166P (1994).
Tian et al., Int. J. Peptide Protein Res., 40(2):119–126 (1992).
Van der Logt et al., Biochemistry, 30(6):1571–1577 (1991).
Van Dijl et al., EMBO J., (8):2819–2828 (1992).
Varadi and Patthy, Biochemistry, 23(9):2108–2112 (1984).
Varadi and Patthy, Biochemistry, 22(10):2440–2446 (1983).
Vedvick et al., J. Ind. Microbiol., 7:197–201 (1991).
Wade et al., Biopolymers, 25:S21–37 (1986).
Wagner et al., Biochem Biophy. Res. Comm., 186:1138–1145 (1992).
Wilson et al., Tetrahedron, 49(17):3655–3663 (1993).
Wun et al., J. Biol. Chem. 263(13):6001–6004 (1988).

KALLIKREIN-INHIBITING "KUNITZ DOMAIN" PROTEINS AND ANALOGUES THEREOF

This application is a 371 of PCT/US95/00299 which is a continuation-in-part of U.S. application Ser. No. 08/208,264, filed Mar. 10, 1994 now abandoned, and is a continuation-in-part of application Ser. No. 08/179,904, filed Jan. 11, 1994, now abandoned, both of which applications are hereby incorporated by reference in their entireties.

BACKGROUND OF THE INVENTION

1. Field of the Invention

This invention relates to novel classes of proteins and protein analogues which bind to and inhibit human plasma kallikrein.

2. Description of the Background Art

Kallikreins are serine proteases found in both tissues and plasma. Plasma kallikrein is involved in contact-activated (intrinsic pathway) coagulation, fibrinolysis, hypotension, and inflammation. (See BHOO92). These effects of kallikrein are mediated through the activities of three distinct physiological substrates: i) Factor XII (coagulation), ii) Pro-urokinase/plasminogen (fibrinolysis), and iii) Kininogens (hypotension and inflammation).

Kallikrein cleavage of kininogens results in the production of kinins, small highly potent bioactive peptides. The kinins act through cell surface receptors present on a variety of cell types. Intracellular heterotrimeric G-proteins link the kinin receptors to second messenger pathways including nitric oxide, adenyl cyclase, phospholipase $A_2$, and phospholipase C. Among the significant physiological activities of kinins are: (i) increased vascular permeability; (ii) vasodilation; (iii) bronchospasm; and (iv) pain induction. Thus, kinins mediate the life-threatening vascular shock and edema associated with bacteremia (sepsis) or trauma, the edema and airway hyperreactivity of asthma, and both inflammatory and neurogenic pain associated with tissue injury. The consequences of inappropriate plasma kallikrein activity and resultant kinin production are dramatically illustrated in patients with hereditary angioedema (HA). HA is due to a genetic deficiency of C1-inhibitor, the principal endogenous inhibitor of plasma kallikrein. Symptoms of HA include edema of the skin, subcutaneous tissues and gastrointestinal tract, and abdominal pain and vomiting. Nearly one-third of HA patients die by suffocation due to edema of the larynx and upper respiratory tract. Kallikrein is secreted as a zymogen (prekallikrein) that circulates as an inactive molecule until activated by a proteolytic event that frees the +$NH_3$-IVGGTNSS... sequence of kallikrein (SEQ ID NO. 1). Human Plasma Prekallikrein is found in Genebank entry Mature plasma Kallikrein contains 619 amino acids. Hydrolysis of the $Arg_{371}$-$Ile_{372}$ peptide bond yields a two-chain proteinase joined by a disulfide bond. The amino-terminal light chain (248 residues) carries the catalytic site.

The main inhibitor of plasma kallikrein (pKA) in vivo is the C1 inhibitor; see SCHM87, pp.27–28. C1 is a serpin and forms an essentially irreversible complex with pKA. Although bovine pancreatic trypsin inhibitor (BPTI) was first said to be a strong pKA inhibitor with $K_i$=320 pM (AUER88), BERN93 indicates that its $K_i$ for pKA is 30 nM (i.e., 30,000 pM). The G36S mutant had a $K_i$ of over 500 nM. Thus, there is a need for a safe kallikrein inhibitor. The essential attributes of such an agent are:

i. Neutralization of relevant kallikrein enzyme(s);
ii. High affinity binding to target kallikreins to minimize dose;
iii. High specificity for kallikrein, to reduce side effects; and
iv. High degree of similarity to a human protein to minimize potential immunogenicity and organ/tissue toxicity.

The candidate target kallikreins to be inhibited are chymotrypsin-homologous serine proteases.

Excessive Bleeding

Excessive bleeding can result from deficient coagulation activity, elevated fibrinolytic activity, or a combination of the two. In most diatheses one must controll the activity of plasmin. However, plasma kallikrein (pKA) is an activator of plasminogen and a potent, selective pKA inhibitor may avert plasminogen activation. The clinically beneficial effect of BPTI in reducing blood loss is thought to result from its inhibition of plasmin ($K_D$~0.3 nM) or of plasma kallikrein ($K_D$~100 nM) or both enzymes. It has been found, however, that BPTI is sufficiently antigenic that second uses require skin testing. Furthermore, the doses of BPTI required to control bleeding are quite high and the mechanism of action is not clear. Some say that BPTI acts on plasmin while others say that it acts by inhibiting plasma kallikrein. FRAE89 reports that doses of about 840 mg of BPTI to 80 open-heart surgery patients reduced blood loss by almost half and the mean amount transfused was decreased by 74%. Miles Inc. has recently introduced Trasylol in the USA for reduction of bleeding in surgery (See Miles product brochure on Trasylol, which is hereby incorporated by reference.) LOHM93 suggests that plasmin inhibitors may be useful in controlling bleeding in surgery of the eye. SHER89 reports that BPTI may be useful in limiting bleeding in colonic surgery.

A kallikrein inhibitor that is much more potent than BPTI and that is almost identical to a human protein domain offers similar therapeutic potential, allows dose to be reduced, and poses less potential for antigenicity.

With recombinant DNA techniques, one may obtain a novel protein by expression of a mutated gene of a parental protein. Several strategies are known for picking mutations to test. One, "protein surgery", involves the introduction of one or more predetermined mutations within the gene of choice. A single polypeptide of completely predetermined sequence is expressed, and its binding characteristics are evaluated.

At the other extreme is random mutagenesis by means of relatively nonspecific mutagens such as radiation and various chemical agents, see Lehtovaara, E.P. Appln. 285,123, or by expression of highly degenerate DNA. It is also possible to follow an intermediate strategy in which some residues are kept constant, others are randomly mutated, and still others are mutated in a predetermined manner. This is called "variegation". See Ladner, et al. U.S. Pat. No. 5,220,409.

DENN94a and DENN94b report selections of Kunitz domains based on APP-I for binding to the complex of Tissue Factor with Factor $VII_a$. They did not use LACI-K1 as parental and did not use pKA as a target. The highest affinity binder they obtained had $K_D$ for their target of about 2 nM. Our first-round selectants for binding to pKA have affinity of about 0.3 nM, and our second round selectants are about at 0.1 nM (=100 pM) or better.

Proteins taken from a. particular species are assumed to be less likely to cause an immune response when injected into individuals of that species. Murine antibodies are highly antigenic in humans. "Chimeric" antibodies having human constant domains and murine variable domains are decidedly less antigenic. So called "humanized" antibodies have human constant domains and variable domains in which the CDRs are taken from murine antibodies while the framework of the variable domains are of human origin. "Humanized" antibodies are much less antigenic than are "chimeric" antibodies. In a "humanized" antibody, fifty to sixty residues of the protein are of non-human origin. The proteins of this invention comprise, in most cases, only about sixty amino acids and usually there are ten or fewer differences between the engineered protein and the parental protein. Although humans do develop antibodies even to human proteins, such as human insulin, such antibodies tend to bind weakly and the often do not prevent the injected protein from displaying its intended biological function. Using a protein from the species to be treated does not guarantee that there will be no immune response. Nevertheless, picking a protein very close in sequence to a human protein greatly reduces the risk of strong immune response in humans.

Kunitz domains are highly stable and can be produced efficiently in yeast or other host organisms. At least ten human Kunitz domains have been reported. Although BPTI was thought at one time to be a potent pKA inhibitor, there are, actually, no human Kunitz domains that inhibits pKA very well. Thus, it is a goal of this invention to provide sequences of Kunitz domain that are both potent inhibitors of pKA and close in sequence to human Kunitz domains.

The use of site-specific mutagenesis, whether nonrandom or random, to obtain mutant binding proteins of improved activity, is known in the art, but does not guarantee that the mutant proteins will have the desired target specificity or affinity. Given the poor anti-kallikrein activity of BPTI, mutation of BPTI or other Kunitz domain proteins would not have been considered, prior to this invention, a preferred method of obtaining a strong binder, let alone inhibitor, of kallikrein.

SUMMARY OF THE INVENTION

This invention relates to novel BPTI-homologous Kunitz domains, especially LACI homologues, which inhibit one or more plasma (and/or tissue) kallikreins, and to the therapeutic and diagnostic use of these novel proteins. In particular, this invention relates to Kunitz domains derived from Kunitz domains of human origin and especially to the first Kunitz domain of LACI; Kunitz domains of human origin are likely to be non-immunogenic in humans. The proteins of this invention inhibit plasma kallikrein (and/or tissue kallikrein) with a $K_D$ of no more than 20 nM, preferably, no more than 5 nM, more preferably, no more than about 300 pM, and most preferably, no more than about 100 pM.

A specific, high affinity inhibitor of plasma kallikrein (and, where needed, tissue kallikrein) will demonstrate significant therapeutic utility in all pathological conditions mediated by kallikrein, and especially those associated with kinins. The therapeutic approach of inhibiting the catalytic production of kinins is considered preferable to antagonism of kinin receptors, since in the absence of kallikrein inhibition, receptor antagonists must compete with continuous kinin generation. Significantly, genetic deficiency of plasma kallikrein is benign and thus, inhibition of plasma kallikrein is likely to be safe. We have recently discovered a lead pKA inhibitor, designated KKII/3#6. This inhibitor is a variant of a naturally occurring human plasma protein Kunitz domain and demonstrates significantly greater kallikrein binding potency than Trasylol. KKII/3#6 has a $K_i$ for kallikrein which is over 100 times that of both wild-type LACI and of BPTI, and is about 300 pM. In contrast, its $K_i$ for plasmin is 10 μM. Proteins KK2/#11 and KK2/#13 are especially preferred pKA inhibitors and have $K_i$<300 pM and probably less than 100 pM. A reversible inhibitor is believed to be of greater utility than an irreversible inhibitor such as the C1 inhibitor.

Transfer of the subsequences that confer pKA binding into other Kunitz domains, particularly human Kunitz domains is disclosed.

The preferred pKA inhibitors of the present invention fullfil one or more of the following desiderata:

1) the inhibitor inhibits plasma kallikrein with a $K_i$ no more than 20 nM, preferably 5 nM or less, more preferably 300 pM or less, and most preferably 100 pM or less, 2) the inhibitor comprises a Kunitz domain meeting the requirements shown in Table 14 with residues numbered by reference to BPTI, 3) the inhibitor has at the Kunitz domain positions 12–21 and 32–39 one of the amino-acid types listed for that position in Table 15, and 4) the inhibitor is substantially homologous to a reference sequence of essentially human origin selected from the group KKII/3#6, KK2/#11, KK2/#13, KK2/#1, KK2/#2, KK2/#3, KK2/#4, KK2/#6, KK2/#7, KK2/#8, KK2/#9, KK2/#10, KK2/#12, KK2conl, Human LACI-K2, Human LACI-K3, Human collagen μ3 KuDom, Human TFPI-2 DOMAIN 1, Human TFPI-2 DOMAIN 2, Human TFPI-2 DOMAIN 3, HUMAN ITI-K1, Human ITI-K2, HUMAN PROTEASE NEXIN-II, Human APP-I, DKI-1.2.1, DKI-1.3.1, DKI-2.1, DKI-3.1.1, DKI-3.2.1, DKI-3.3.1, DKI-4.1.1, DKI-4.2.1, DKI-4.2.2, DKI-5.1, and DKI-6.1

Nomenclature

Herein, affinities are stated as $K_D$ ($K_D(A,B)=[A][B]/[A-B]$). A numerically smaller $K_D$ reflects higher affinity. For the purposes of this invention, a "kallikrein inhibiting protein" is one that binds and inhibits a specified kallikrein with $K_i$ of about 20 nM or less. "Inhibition" refers to blocking the catalytic activity of kallikrein and so is measurable in vitro in assays using chromogenic or fluorogenic substrates or in assays involving macromolecules.

Amino-acid residues are discussed in three ways: full name of the amino acid, standard three-letter code, and standard single-letter code. The text uses full names and three-letter code where clarity requires.

| A = Ala | G = Gly | M = Met | S = Ser |
|---------|---------|---------|---------|
| C = Cys | H = His | N = Asn | T = Thr |
| D = Asp | I = Ile | P = Pro | V = Val |
| E = Glu | K = Lys | Q = Gln | W = Trp |
| F = Phe | L = Leu | R = Arg | Y = Tyr |

For the purposed of this invention, "substantially homologous" sequences are at least 51%, more preferably at least 80%, identical, over any specified regions. For this invention, "substantially homologous" includes exact identity. Sequences would still be "substantially homologous" if within one region of at least 20 amino acids they are sufficiently similar (51% or more) but outside the region of comparison they differed totally. An insertion of one amino acid in one sequence relative to the other counts as one mismatch. Most preferably, no more than six residues, other than at termini, are different. Preferably, the divergence in sequence, particularly in the specified regions, is in the form of "conservative modifications".

"Conservative modifications" are defined as (a) conservative substitutions of amino acids as defined in Table 9; and (b) single or multiple insertions or deletions of amino acids at termini, at domain boundaries, in loops, or in other segments of relatively high mobility.

Preferably, except at termini, no more than about six amino acids are inserted or deleted at any locus, and the modifications are outside regions known to contain important binding sites.

Kunitz Domains

Herein, "Kunitz domain" and "KuDom" are used interchangeably to mean a homologue of BPTI (not of the Kunitz soya-bean trypsin inhibitor). A KuDom is a domain of a protein having at least 51 amino acids (and up to about 61 amino acids) containing at least two, and preferably three, disulfides. Herein, the residues of all Kunitz domains are numbered by reference to BPTI (i.e. residues 1–58, amino-acid sequence in Table 2). Thus the first cysteine residue is residue 5 and the last cysteine is 55. An amino-acid sequence shall, for the purposes of this invention, be deemed a Kunitz domain if it can be aligned, with three or fewer mismatches, to the sequence shown in Table 14. An insertion or deletion of one residue shall count as one mismatch. In Table 14, "x" matches any amino acid and "X" matches the types listed for that position Disulfide bonds link at least two of: 5 to 55, 14 to 38, and 30 to 51. The number of disulfides may be reduced by one, but none of the standard cysteines shall be left unpaired. Thus, if one cysteine is changed, then a compensating cysteine is added in a suitable location or the matching cysteine is also replaced by a non-cysteine (the latter being generally preferred). For example, *Drosophila funebris* male accessory gland protease inhibitor has no cysteine at position 5, but has a cysteine at position -1 (just before position 1); presumably this forms a disulfide to $CYS_{55}$. If $Cys_{14}$ and $Cys_{38}$ are replaced, the requirement of $Gly_{-12}$, (Gly or Ser)$_{37}$, and $Gly_{36}$ are dropped. From zero to many residues, including additional domains (including other KuDoms), can be attached to either end of a Kunitz domain.

DETAILED DESCRIPTION OF THE PREFERRED EMBODIMENTS

Protease inhibitors, such as Kunitz domains, function by binding into the active site of the protease so that a peptide bond (the "scissile bond") is: 1) not cleaved, 2) cleaved very slowly, or 3) cleaved to no effect because the structure of the inhibitor prevents release or separation of the cleaved segments. In Kunitz domains, disulfide bonds act to hold the protein together even if exposed peptide bonds are cleaved. From the residue on the amino side of the scissile bond, and moving away from the bond, residues are conventionally called P1, P2, P3, etc. Residues that follow the scissile bond are called P1', P2', P3', etc. (SCHE67, SCHE68). It is generally accepted that each serine protease has sites (comprising several residues) S 1, S2, etc. that receive the side groups and main-chain atoms of residues P1, P2, etc. of the substrate or inhibitor and sites S1', S2', etc. that receive the side groups and main-chain atoms of P1', P2', etc. of the substrate or inhibitor. It is the interactions between the S sites and the P side groups and main chain atoms that give the protease specificity with respect to substrates and the inhibitors specificity with respect to proteases. Because the fragment having the new amino terminus leaves the protease first, many worker designing small molecule protease inhibitors have concentrated on compounds that bind sites S1, S2, S3, etc.

LASK80 reviews protein protease inhibitors. Some inhibitors have several reactive sites on one polypeptide chain, and these domains usually have different sequences, specificities, and even topologies. It is known that substituting amino acids in the $P_5$ to $P_5'$ region influences the specificity of an inhibitor. Previously, attention has been focused on the P1 residue and those very close to it because these can change the specificity from one enzyme class to another. LASK80 suggests that among KuDoms, inhibitors with P1=Lys or Arg inhibit trypsin, those with P1=Tyr, Phe, Trp, Leu and Met inhibit chymotrypsin, and those with P1=Ala or Ser are likely to inhibit elastase. Among the Kazal inhibitors, LASK80 continues, inhibitors with P1=Leu or Met are strong inhibitors of elastase, and in the Bowman-Kirk family elastase is inhibited with P1=Ala, but not with P1=Leu. Such limited changes do not provide inhibitors of truly high affinity (i.e. better than 1 to 10 nM).

KuDoms are defined above. The 3D structure (at high resolution) of BPTI (the archetypal Kunitz domain) is known. One of the X-ray structures is deposited in the Brookhaven Protein Data Bank as "6PTI"]. The 3D structure of some BPTI homologues (EIGE90, HYNE90) are known. At least seventy KuDom sequences are known. Known human homologues include three KuDoms of LACI (WUNT88, GERA89, NOVO89), two KuDoms of Inter-α-Trypsin Inhibitor, APP-I (KIDO88), a KuDom from collagen, and three KuDoms of TFPI-2 (SPRE94).

LACI

Lipoprotein-associated coagulation inhibitor (LACI) is a human serum phosphoglycoprotein with a molecular weight of 39 kDa (amino-acid sequence in Table 1) containing three KuDoms. We refer hereinafter to the protein as LACI and to the Kunitz domains thereof as LACI-K1 (residues 50 to 107), LACI-K2 (residues 121 to 178), and LACI-K3 (213 to 270). The cDNA sequence of LACI is reported in WUNT88. GIRA89 reports mutational studies in which the P1 residues of each of the three KuDoms were altered. LACI-K1 inhibits Factor VIIa ($F.VII_a$) when $F.VII_a$ is complexed to tissue factor and LACI-K2 inhibits Factor $X_a$. It is not known whether LACI-K3 inhibits anything. Neither LACI nor any of the KuDoms of LACI is a potent plasma kallikrein inhibitor.

In one preferred embodiment of this invention, KuDoms are substantially homologous with LACI-K1, but differ in ways that confer strong plasma kallikrein inhibitory activity discussed below. Other KuDoms of this invention are homologous to other naturally-occurring KuDoms, particularly to other human KuDoms. For use in humans, the proteins of this invention are designed to be highly similar in sequence to one or another human KuDom to reduce the risk of causing an immune response.

Variegation of a protein is typically achieved by preparing a correspondingly variegated mixture of DNA (with variable codons encoding variable residues), cloning it into suitable vectors, and expressing the DNA in suitable host cells. For any given protein molecule of the library, the choice of amino acid at each variable residue, subject to the above constraints, is random, the result of the happenstance of which DNA expressed that protein molecule.

FIRST LACI-K1 LIBRARY SCREENED FOR pKA BINDING

Applicants have screened a first large library of LACI-K1 domains (patern of variegation is shown in Table 21), with the results shown in Table 3. In Table 3, "Library Residues" are those permitted to occur, randomly, at that position, in the library, and "Preferred Residues" are those appearing at that position in at least one of the 10 variants identified as binding to human kallikrein.

At residues 13, 16, 17, 18, 31, and 32, the selections are very strong. At position 34, the selection for either SER or THR is quite strong. At position 39, the selection for GLY is strong. Position 19 seems to be rather tolerant.

It should be appreciated that Applicants have not sequenced all of the positive isolates in this or other the libraries herein disclosed, that some of the possible mutant proteins may not have been present in the library in detectable amounts, and that, at some positions, only some of the possible amino acids were intended to be included in the library.

SECOND LIBRARY OF LACI-K1 and SELECTION OF NEW KALLIKREIN INHIBITORS

Applicants prepared a second LACI-K1 library as shown in Table 750. This library utilized the observation of the first selection and allows variability at positions 10, 11, 13, 15, 16, 17, 18, 19, and 21. The residues at positions 34 and 39 were fixed at $S_{34}$ and $G_{39}$. Selectants KK2/#1 through KK2/#13, as shown in Table 2 were obtained in the same manner as described in the Example section for the first screeneing. Applicants prepared the proteins KK2/#11 and KK2/#13 in *S. cerevisiae* in the Matα system described herein. Preliminary measurements indicate that these proteins are very potent pKA inhibitors with K less than 300 pM and probably less than 100 pM.

Using the selected sequences and the binding data of selected KuDoms, we can write a recipe for a high-affinity pKA-inhibiting KuDom that can be applied to other human KuDom parentals. First, the KuDom must meet the requirements in Table 14. The substitutions shown in Table 15 are likely to confer high-affinity pKA inhibitory activity on any KuDom. Thus a protein that contains a sequence that is a KuDom, as shown in Table 14, and that contains at each of the position 12–21 and 32–39 an amino-acid type shown in Table 15 for that position is likely to be a potent inhibitor of human pKA. More preferably, the protein would have an amino-acid type shown in Table 15 for all of the positions listed in Table 15. To reduce the potential for immune response, one should use one or another human KuDom as parental protein to give the sequence outside the binding region.

It is likely that a protein that comprises an amino-acid sequence that is substantially homologous to one of KK2/#13, KK2/#11, or KKII/3#6 from residue 5 through residue 55 (as shown in Table 2) and is identical to one of KK2/#13, KK2/#11, or KKII/3#6 at positions 13–19, 31, 32, 34, and 39 will inhibit human pKA with a $K_i$ of 5 nM or less. KK2/#13, KK2/#11, and KKII/3#6 differs from LACI-K1 at 10, 8, and 7 positions respectively. It is not clear that these substitutions are equally important in fostering pKA binding and inhibition. From the known pKA inhibitors listed, one can prepare a series of molecules that are progressively reverted toward LACI-K1. It is expected that the molecules will show less affinity for pKA but also less potential for antigenicity. A person skilled in the art can pick a protein of sufficient potency and low immunogenicity from this collection. It is also possible that substitutions in one of the listed pKA inhibitors by amino acids that differ from LACI-K1 can reduce the immunogenicity without reducing the affinity for pKA to a degree that makes the protein unsuitable for use as a drug.

DESIGNED KuDom PKA Inhibitors

Hereinafter, "DKI" will mean a "Designed PKA Inhibitor" that are KuDoms that incorporate amino-acid sequence information from the SPI series of molecules, especially KK2/#13, KK2/#11, or KKII/3#6. Sequences of several DKIs and their parental proteins are given in Table 2.

Hereinafter, the statement "the mutations $X_{nn}Y_1$, $X_{nn}Y_2$, ... may not be needed" means that each of the mutations might be separately found to be unnecessary. That is, the list is not to be taken as a block to be applied together, but as a list of things to be tested. Similarly, the lists of additional mutations are to be tested singly.

Protein DKI-1.2.1 is based on human LACI-K2 and shown in Table 2. The mutations P11G, I13R, Y17A, I18H, T19P, Y21W, R32E, K34S, and L39G are likely to confer high affinity for pKA. Some of these substitutions may not be necessary; in particular, P11G and T19P may not be necessary. Other mutations that might improve the pKA affinity include E9A, D10E, G16A, Y21F, and L39E.

Protein DKI-1.3.1 (Table 2) is based on human LACI-K3. The mutations R11D, L13P, N17A, E18H, N19P, R31E, K34S, and S36G are intended to confer high affinity for pKA. Some of these substitutions may not be necessary; in particular, N19P may not be necessary. Other changes that might improve $K_D$ include D10E, F21W and G39E.

Protein DKI-2.1 (Table 2) is a based on the human collagen α3 KuDom. The mutations D16A, F17A, I18H, R32E, and W34S are likely to confer high affinity for pKA. Some of these substitutions may not be necessary; in particular, R32E may not be necessary. Other mutations that might improve the pKA affinity include K9A, D10E, D 16G, K20R, R32T, W34V, and G39E.

DKI-3.1.1 (Table 2) is derived from Human TFPI-2 domain 1. The exchanges Y11G, L17A, L18H, R31E, and L34S are likely to confer high affinity for pKA. The mutation L34S may not be needed. Other mutations that might foster pKA binding include Y21W, Y21F, Q32E, L34T, L34I, and E39G.

DKI-3.2.1 (Table 2) is derived from Human TFPI-2 domain 2. This parental domain contains insertions after residue 9 (one residue) and 42 (two residues). The mutations E15R, G16A, S 17A, T18H,E19P, K32T, and F34V are intended to confer affinity for pKA. If one needs a pKA inhibitor based on TFPI domain 2, a preferred route is to make a library of domains allowing the substitutions given and many others and then select binders.

DKI-3.3.1 (Table 2) is derived from human TFPI-2, domain 3. The substitutions L13H, S 15R, and N17A are likely to confer high affinity for pKA. Other mutations that might foster pKA binding include D10E, T19Q, Y21W, T36G, and G39E.

DKI-4.1.1 (Table 2) is from human ITI-K1 by assertion of S10D, M15R, M17A, T18H, Q34S, and M39G. The mutations M39G and Q34V may not be necessary. Other mutations that should foster pKA binding include: G16A, M17N, S19Q, Y21W, and Y21F.

DKI-4.2.1 (Table 2) is from human ITI-K2 through the mutations V10D, R11D, F17A, I18H, V31E, L32E, P34S, and Q39E. The mutations V31E, L32E, and Q39E might not be necessary. Other mutation that should foster pKA binding include: V10E, Q19P, L20R, W21F, P34I, and Q39G. DKI-4.2.2 has eight mutations: V10D, R11D, F17A, I18H, L20R, V31E, L32E, and P34S.

DKI-5.1 is derived from human APP-I (also known as Protease Nexin-II) by mutations M17A, I18H, S19P, A31E, and P32E and is likely to be a potent pKA inhibitor. The mutations S19P, A3 1E, and P32E many not be needed. Other mutations that might foster pKA binding include T11D.

DKI-6.1 is derived from the HKI B9 KuDom (NORR93) by the five substitutions: K11D, Q15R, T16A, M17A, M18H, T19P, and L32E. DKI-6.1 is likely to be a potent pKA inhibitor. The mutations L32E, and T19P might not be needed.

Although BPTI is not an especially good pKA inhibitor, it could be made into one. DKI-7.1 is derived from BPTI by the mutations Y10E, K15R, R17A, R18H, I19P, Q31E, T32E, and R39E which is likely to increase the affinity for pKA. The mutations Y10E, K15R, I19P, Q31E, T32E, and R39E may not be needed; the really important mutations are R17A and R18H.

MODIFICARION OF KUNITZ DOMAINS

KuDoms are quite small; if this should cause a pharmacological problem, such as excessively quick elimination from circulation, two or more such domains may be joined. A preferred linker is a sequence of one or more amino acids. A preferred linker is one found between repeated domains of a human protein, especially the linkers found in human BPTI homologues, one of which has two domains (BALD85, ALBR83a, ALBR83b) and another of which has three (WUNT88). Peptide linkers have the advantage that the entire protein may then be expressed by recombinant DNA techniques. It is also possible to use a nonpeptidyl linker, such as one of those commonly used to form immunogenic conjugates. An alternative means of increasing the serum residence of a BPTI-like KuDom is to link it to polyethyleneglycol, so called PEGylation (DAVI79).

WAYS TO IMPROVE SPECIFICITY OF, FOR EXAMPLE, KKII/3#7, KK2/#11, AND KK2/#13 FOR PLASMA KALLIKREIN:

Because we have made a large part of the surface of KKII/3#6, KK2/#11, and KK2/#13 complementary to the surface of pKA, $R_{15}$ is not essential for specific binding to pKA. Many of the enzymes in the clotting and fibrinolytic pathways cut preferentially after Arg or Lys. Not having a basic residue at the P1 position may give rise to greater specificity. The variant KKII/3#7-K15A (shown in Table 27), having an ALA at P1, is likely to be a good pKA inhibitor and may have higher specificity for pKA relative to other proteases than doesKKII/3#7. The affinity of KKII/3#7-K15A for pKA is likely to be less than the affinity of KKII/3#7 for pKA, but the loss of affinity for other Arg/Lys-preferring enzymes is likely to be greater and, in many applications, specificity is more important than affinity. Other mutants that are likely to have good affinity and very high specificity include KK2/#13-R15A and KK2/#11-R15S. This approach could be applied to other high-affinity pKA inhibitors.

MODE OF PRODUCTION

The proteins of this invention may be produced by any conventional technique, including (a) nonbiological synthesis by sequential coupling of component amino acids, (b) production by recombinant DNA techniques in a suitable host cell, and (c) removal of undesired sequences from LACI and coupling of synthetic replacement sequences The proteins disclosed herein are preferably produced, recombinantly, in a suitable host, such as bacteria from the genera Bacillus, Escherichia, Salmonella, Erwinia, and yeasts from the genera Hansenula, Kluyveromyces, Pichia, Rhinosporidium, Saccharomyces, and Schizosaccharomyces, or cultured mammalian cells such as COS-1. The more preferred hosts are microorganisms of the species *Pichia pastoris, Bacillus subtilis, Bacillus brevis, Saccharomyces cerevisiae, Escherichia coli* and *Yarrowia lipolytica*. Any promoter, regulatable or constitutive, which is functional in the host may be used to control gene expression.

Preferably the proteins are secreted. Most preferably, the proteins are obtained from conditioned medium. It is not required that the proteins described herein be secreted. Secretion is the preferred route because proteins are more likely to fold correctly, can be produced in conditioned medium with few contaminants, and are less likely to be toxic to host cells. Secretion is not required.

Unless there is a specific reason to include glycogroups, we prefer proteins designed to lack N-linked glycosylation sites to reduce potential for antigenicity of glycogroups and so that equivalent proteins can be expressed in a wide variety of organisms including: 1) *E. coli*, 2) *B. subtilis*, 3) *P. pastoris*, 4) *S. cerevisiae*, and 5) mammalian cells.

Several means exist for reducing the problem of host cells producing proteases that degrade the recombinant product; see, inter alia BANE90 and BANE91. VAND92 reports that overexpression of the *B. subtilis* signal peptidase in *E. coli*, leads to increased expression of a heterologous fusion protein. ANBA88 reports that addition of PMSF (a serine proteases inhibitor) to the culture medium improved the yield of a fusion protein.

Other factors that may affect production of these and other proteins disclosed herein include: 1) codon usage (optimizing codons for the host is preferred), 2) signal sequence, 3) amino-acid sequence at intended processing sites, presence and localization of processing enzymes, deletion, mutation, or inhibition of various enzymes that might alter or degrade the engineered product and mutations that make the host more permissive in secretion (permissive secretion hosts are preferred).

Reference works on the general principles of recombinant DNA technology include Watson et al., Molecular Biology of the Gene, Volumes I and II, The Benjamin/Cummings Publishing Company, Inc., Menlo Park, Calif. (1987); Darnell et al., Molecular Cell Biology, Scientific American Books, Inc., New York, N.Y. (1986); Lewin, Genes II, John Wiley & Sons, New York, N.Y. (1985); Old, et al., Principles of Gene Manipulation: An Introduction to Genetic Engineering, 2d edition, University of California Press, Berkeley, Calif. (1981); Sambrook et al, Molecular Cloning: A Laboratory Manual, Cold Spring Harbor Laboratory, Cold Spring Harbor, N.Y. (1989); and Ausubel et al, Current Protocols in Molecular Biology, Wiley Interscience, N.Y., (1987, 1992). These references are herein entirely incorporated by reference as are the references cited therein.

PREPARATION OF PEPTIDES

Chemical polypeptide synthesis is a rapidly evolving area in the art, and methods of solid phase polypeptide synthesis are well-described in the following references, hereby entirely incorporated by reference: (Merrifield, *J Amer Chem Soc* 85:2149–2154 (1963); Merrifield, *Science* 232:341–347 (1986); Wade et al., *Biopolymers* 25:S21–S37 (1986); Fields, *Int J Polypeptide Prot Res* 35:161 (1990); MilliGen Report Nos. 2 and 2a, Millipore Corporation, Bedford, Mass, 1987) Ausubel et al, supra, and Sambrook et al, supra. Tan and Kaiser (*Biochemistry*, 1977, 16:1531–41) synthesized BPTI and a homologue eighteen years ago.

As is known in the art, such methods involve blocking or protecting reactive functional groups, such as free amino, carboxyl and thio groups. After polypeptide bond formation, the protective groups are removed. Thus, the addition of each amino acid residue requires several reaction steps for protecting and deprotecting. Current methods utilize solid phase synthesis, wherein the C-terminal amino acid is covalently linked to an insoluble resin particles that can be filtered. Reactants are removed by washing the resin particles with appropriate solvents using an automated machine. Various methods, including the "tBoc" method and the "Fmoc" method are well known in the art. See, inter alia, Atherton et al., *J Chem Soc Perkin Trans* 1:538–546 (1981) and Sheppard et al, *Int J Polypeptide Prot Res* 20:451–454 (1982).

ASSAYS FOR PLASMA KALLIKREIN BINDING AND INHIBITION

Any suitable method may be used to test the compounds of this invention. Scatchard (*Ann NY Acad Sci* (1949) 51:660–669) described a classical method of measuring and analyzing binding which is applicable to protein binding. This method requires relatively pure protein and the ability to distinguish bound protein from unbound.

A second appropriate method of measuring $K_D$ is to measure the inhibitor activity against the enzyme. If the $K_D$ to be measured is in the 1 nM to 1 μM range, this method requires chromogenic or fluorogenic substrates and tens of micrograms to milligrams of relatively pure inhibitor. For the proteins of this invention, having $K_D$ in the range 5 nM to 50 pM, nanograms to micrograms of inhibitor suffice. When using this method, the competition between the inhibitor and the enzyme substrate can give a measured $K_i$ that is higher than the true $K_i$. Measurement reported here are not so corrected because the correction would be very small and the any correction would reduce the $K_i$. Here, we use the measured $K_i$ as a direct measure of $K_D$.

A third method of determining the affinity of a protein for a second material is to have the protein displayed on a genetic package, such as M13, and measure the ability of the protein to adhere to the immobilized "second material". This method is highly sensitive because the genetic packages can be amplified. We obtain at least semiquantitative values for the binding constants by use of a pH step gradient. Inhibitors of known affinity for the protease are used to establish standard profiles against which other phage-displayed inhibitors are judged. Any other suitable method of measuring protein binding may be used.

Preferably, the proteins of this invention have a $K_D$ for pKA of at most about 5nM, more preferably at most about 300 pM, and most preferably 100 pM or less. Preferably, the binding is inhibitory so that $K_i$ is the same as $K_D$. The $K_i$ of KKII/3#6 is about 300 pM and the $K_i$s of KK2/#11 and KK2/#13 are less than 300 pM and probably less than 100 pM.

Pharmaceutical Methods and Preparations

The preferred subject of this invention is a mammal. The invention is particularly useful in the treatment of humans, but is suitable for veternary applications too.

Herein, "protection" includes "prevention", "suppression", and "treatment". "Prevention" involves administration of drug prior to the induction of disease. "Suppression" involves administration of drug prior to the clinical appearance of disease. "Treatment" involves administration of drug after the appearance of disease.

In human and veterinary medicine, it may not be possible to distinguish between "preventing" and "suppressing" since the inductive event(s) may be unknown or latent, or the patient is not ascertained until after the occurrence of the inductive event(s). We use the term "prophylaxis" as distinct from "treatment" to encompass "preventing" and "suppressing". Herein, "protection" includes "prophylaxis". Protection need not be absolute to be useful.

Proteins of this invention may be administered, by any means, systemically or topically, to protect a subject against a disease or adverse condition. For example, administration of such a composition may be by any parenteral route, by bolus injection or by gradual perfusion. Alternatively, or concurrently, administration may be by the oral route. A suitable regimen comprises administration of an effective amount of the protein, administered as a single dose or as several doses over a period of hours, days, months, or years.

The suitable dosage of a protein of this invention may depend on the age, sex, health, and weight of the recipient, kind of concurrent treatment, if any, frequency of treatment, and the desired effect. However, the most preferred dosage can be tailored to the individual subject, as is understood and determinable by one of skill in the art, without undue experimentation by adjustment of the dose in ways known in the art.

For methods of pre clinical and clinical testing of drugs, including proteins, see, e.g., Berkow et al, eds., The Merck Manual, 15th edition, Merck and Co., Rahway, N.J., 1987; Goodman et al, eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985), which references and references cited there are hereby incorporated by reference.

In addition to a protein here disclosed, a pharmaceutical composition may contain pharmaceutically acceptable carriers, excipients, or auxiliaries. See, e.g., Berker, supra, Goodman, supra, Avery, supra and Ebadi, supra.

In Vitro Diagnostic Methods and Reagents

Proteins of this invention may be applied in vitro to any suitable sample that might contain plasma kallikrein to measure the pKA present. To do so, the assay must include a Signal Producing System (SPS) providing a detectable signal that depends on the amount of pKA present. The signal may be detected visually or instrumentally. Possible signals include production of colored, fluorescent, or luminescent products, alteration of the characteristics of absorption or emission of radiation by an assay component or product, and precipitation or agglutination of a component or product.

The component of the SPS most intimately associated with the diagnostic reagent is called the "label". A label may be, e.g., a radioisotope, a fluorophore, an enzyme, a co-enzyme, an enzyme substrate, an electron-dense compound, or an agglutinable particle. A radioactive isotope can be detected by use of, for example, a γ counter or a scintillation counter or by autoradiography. Isotopes which are particularly useful are $^3$H, $^{125}$I, $^{131}$I, $^{35}$S, $^{14}$C, and, preferably, $^{125}$I. It is also possible to label a compound with a fluorescent compound. When the fluorescently labeled compound is exposed to light of the proper wave length, its presence can be detected. Among the most commonly used fluorescent labelling compounds are fluorescein isothiocyanate, rhodamine, phycoerythrin, phycocyanin, allophycocyanin, o-phthaldehyde, and fluorescamine. Alternatively, fluorescence-emitting metals, such as $^{125}$Eu or other lanthanide, may be attached to the binding protein using such metal chelating groups as diethylenetriaminetetraacetic acid or ethylenediamine-tetraacetic acid. The proteins also can be detectably labeled by coupling to a chemi-numinescent compound, such as luminol, isolumino, theromatic acridinium ester, imidazole, acridinium salt, and oxalate ester. Likewise, a bioluminescent compound, such as luciferin, luciferase and aequorin, may be used to label the binding protein. The presence of a bioluminescent protein is determined by detecting the presence of luminescence. Enzyme labels, such as horseradish peroxidase and alkaline phosphatase, are preferred.

There are two basic types of assays: heterogeneous and homogeneous. In heterogeneous assays, binding of the affinity molecule to analyte does not affect the label; thus, to determine the amount of analyte, bound label must be separated from free label. In homogeneous assays, the interaction does affect the activity of the label, and analyte can be measured without separation.

In general, a kallikrein-binding protein (KBP) may be used diagnostically in the same way that an anti-pKA antibody is used. Thus, depending on the assay format, it may be used to assay pKA, or, by competitive inhibition, other substances which bind pKA.

The sample will normally be a biological fluid, such as blood, urine, lymph, semen, milk, or cerebrospinal fluid, or a derivative thereof, or a biological tissue, e.g., a tissue section or homogenate. The sample could be anything. If the sample is a biological fluid or tissue, it may be taken from a human or other mammal, vertebrate or animal, or from a plant. The preferred sample is blood, or a fraction or derivative thereof In one embodiment, the pKA-binding protein (KBP) is immobilized, and pKA in the sample is allowed to compete with a known quantity of a labeled or specifically labelable pKA analogue. The "pKA analogue" is a molecule capable of competing with pKA for binding to the KBP, which includes pKA itself It may be labeled already, or it may be labeled subsequently by specifically binding the label to a moiety differentiating the pKA analogue from pKA. The phases are separated, and the labeled pKA analogue in one phase is quantified.

In a "sandwich assay", both an insolubilized pKA-binding agent (KBA), and a labeled KBA are employed. The pKA analyte is captured by the insolubilized KBA and is tagged by the labeled KBA, forming a tertiary complex. The reagents may be added to the sample in any order. The KBAs may be the same or different, and only one KBA need be a KBP according to this invention (the other may be, e.g., an antibody). The amount of labeled KBA in the tertiary complex is directly proportional to the amount of pKA in the sample.

The two embodiments described above are both heterogeneous assays. A homogeneous assay requires only that the label be affected by the binding of the KBP to pKA. The pKA analyte may act as its own label if a pKA inhibitor is used as a diagnostic reagent.

A label may be conjugated, directly or indirectly (e.g., through a labeled anti-KBP antibody), covalently (e.g. with SPDP) or noncovalently, to the pKA-binding protein, to produce a diagnostic reagent. Similarly, the pKA binding protein may be conjugated to a solid phase support to form a solid phase ("capture") diagnostic reagent. Suitable supports include glass, polystyrene, polypropylene, polyethylene, dextran, nylon, amylases, and magnetite. The carrier can be soluble to some extent or insoluble for the purposes of this invention. The support material may have any structure so long as the coupled molecule is capable of binding pKA.

In Vivo Diagnostic Uses

A Kunitz domain that binds very tightly to pKA can be used for in vivo imaging. Diagnostic imaging of disease foci was considered one of the largest commercial opportunities for monoclonal antibodies, but this opportunity has not been achieved. Despite considerable effort, only two monoclonal antibody-based imaging agents have been approved. The disappointing results obtained with monoclonal antibodies is due in large measure to:

i) Inadequate affinity and/or specificity;
ii) Poor penetration to target sites;
iii) Slow clearance from nontarget sites;
iv) Immunogenicity (most are murine); and
v) High production cost and poor stability.

These limitations have led most in the diagnostic imaging field to begin to develop peptide-based imaging agents. While potentially solving the problems of poor penetration and slow clearance, peptide-based imaging agents are unlikely to possess adequate affinity, specificity and in vivo stability to be useful in most applications.

Engineered proteins are uniquely suited to the requirements for an imaging agent. In particular the extraordinary affinity and specificity that is obtainable by engineering small, stable, human-origin protein domains having known in vivo clearance rates and mechanisms combine to provide earlier, more reliable results, less toxicity/side effects, lower production and storage cost, and greater convenience of label preparation. Indeed, it should be possible to achieve the goal of realtime imaging with engineered protein imaging agents. Thus, a Kallikrein-binding protein, e.g., KKII/3#6, KK2/#11, and KK2/#13 may be used for localizing sites of excessive pKA activity.

Radio-labelled binding protein may be administered to the human or animal subject. Administration is typically by injection, e.g., intravenous or arterial or other means of administration in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as guides.

Typically, the imaging is carried out on the whole body of the subject, or on that portion of the body or organ relevant to the condition or disease under study. The radio-labelled binding protein has accumulated. The amount of radio-labelled binding protein accumulated at a given point in time in relevant target organs can then be quantified.

A particularly suitable radio-detecting device is a scintillation camera, such as a γ camera. The detection device in the camera senses and records (and optional digitizes) the radioactive decay. Digitized information can be analyzed in any suitable way, many of which are known in the art. For example, a time-activity analysis can illustrate uptake through clearance of the radio-labelled binding protein by the target organs with time.

Various factors are taken into consideration in picking an appropriate radioisotope. The isotope is picked: to allow good quality resolution upon imaging, to be safe for diagnostic use in humans and animals, and, preferably, to have a short half-life so as to decrease the amount of radiation received by the body. The radioisotope used should preferably be pharmacologically inert, and the quantities administered should not have substantial physiological effect. The binding protein may be radio-labelled with different isotopes of iodine, for example $^{123}$I, $^{125}$I, or $^{131}$I (see, for example, U.S. Pat. No. 4,609,725). The amount of labeling must be suitably monitored.

In applications to human subjects, it may be desirable to use radioisotopes other than $^{125}$I for labelling to decrease the total dosimetry exposure of the body and to optimiize the detectability of the labelled molecule. Considering ready clinical availability for use in humans, preferred radio-labels include: $^{99m}$Tc, $^{67}$Ga, $^{68}$Ga, $^{90}$Y, $^{111}$In, $^{113m}$In, $^{123}$I, $^{186}$Re, $^{188}$Re or $^{211}$At. Radio-labelled protein may be prepared by various methods. These include radio-halogenation by the chloramine-T or lactoperoxidase method and subsequent purification by high pressure liquid chromatography, for example, see Gutkowska et al in "Endocrinology and Metabolism Clinics of America: (1987) 16 (1): 183. Other methods of radio-labelling can be used, such as IODO-BEADS™.

A radio-labelled protein may be administered by any means that enables the active agent to reach the agent's site of action in a mammal. Because proteins are subject to digestion when administered orally, parenteral administration, i.e., intravenous subcutaneous, intramuscular, would ordinarily be used to optimize absorption.

High-affinity, high-specificity inhibitors are also useful for in vitro diagnostics of excess human pKA activity.

Other Uses

The kallikrein-binding proteins of this invention may also be used to purify kallikrein from a fluid, e.g., blood. For this, the KBP is preferably immobilized on a support. Such supports, include those already mentioned as useful in preparing solid phase diagnostic reagents.

Proteins can be used as molecular weight markers for reference in the separation or purification of proteins. Proteins may need to be denatured to serve as molecular weight markers. A second general utility for proteins is the use of hydrolyzed protein as a nutrient source. Proteins may also be used to increase the viscosity of a solution.

The proteins of this invention may be used for any of the foregoing purposes, as well as for therapeutic and diagnostic purposes as discussed further earlier in this specification.

EXAMPLE 1:

Construction of First LACI-K1 Library

A synthetic oligonucleotide duplex having NsiI- and MluI-compatible ends was cloned into a parental vector (LACI:III) previously cleaved with the above two enzymes. The resultant ligated material was transfected by electroporation into XLIMR ($F^-$) *Escherichia coli* strain and plated on Amp plates to obtain phage-generating $Ap^R$ colonies. The variegation scheme for Phase 1 focuses on the P1 region, and affected residues 13, 16, 17, 18 and 19. It allowed for $6.6 \times 10^5$ different DNA sequences ($3.1 \times 10^5$ different protein sequences). The library obtained consisted of $1.4 \times 10^6$ independent cfu's which is approximately a two fold representation of the whole library. The phage stock generated from this plating gave a total titer of $1.4 \times 10^{13}$ pfu's in about 3.9 ml, with each independent clone being represented, on average, $1 \times 10^7$ in total and $2.6 \times 10^6$ times per ml of phage stock.

To allow for variegation of residues 31, 32, 34 and 39 (phase II), synthetic oligonucleotide 5 duplexes with MluI- and BstEII- compatible ends were cloned into previously cleaved $R_f$ DNA derived from one of the following i) the parental construction, ii) the phase I library, or iii) display phage selected from the first phase binding to a given target.

The variegation scheme for phase II allows for 4096 different DNA sequences (1600 different protein sequences) due to alterations at residues 31, 32, 34 and 39. The final phase II variegation is dependent upon the level of variegation remaining following the three rounds of binding and elution with a given target in phase I.

The combined possible variegation for both phases equals $2.7 \times 10^8$ different DNA sequences or $5.0 \times 10^7$ different protein sequences. When previously selected display phage are used as the origin of $R_f$ DNA for the phase II variegation, the final level of variegation is probably in the range of $10^5$ to $10^6$.

EXAMPLE 2:

Screening of LACI (K1) Library for Binding to Kallikrein

The overall scheme for selecting a LACI-K1 variant to bind to a given protease involves incubation of the phage-display library with the kallikrein-beads of interest in a buffered solution (PBS containing 1 mg/ml BSA) followed by washing away the unbound and poorly retained display-phage variant with PBS containing 0.1% Tween 20. Kallikrein beads were made by coupling human plasma Kallikrein (Calbiochem, San Diego, Calif., #420302) to agarose beads using Reactigel (6x) (Pierce, Rockford, II. #202606). The more strongly bound display-phage are eluted with a low pH elution buffer, typically citrate buffer (pH 2.0) containing 1 mg/ml BSA, which is immediately neutralized with Tris buffer to pH 7.5. This process constitutes a single round of selection.

The neutralized eluted display-phage can be either used:

i) to inoculate an $F^+$ strain of *E. coli* to generate a new display-phage stock, to be used for subsequent rounds of selection (so-called conventional screening), or ii) be used directly for another immediate round of selection with the protease beads (so-called quick screening).

Typically, three rounds of either method, or a combination of the two, are performed to give rise to the final selected display-phage from which a representative number are sequenced and analyzed for binding properties either as pools of display-phage or as individual clones.

Two phases of selection were performed, each consisting of three rounds of binding and elution. Phase I selection used the phase I library (variegated residues 13, 16, 17, 18, and 19) which went through three rounds of binding and elution against a target protease giving rise to a subpopulation of clones. The $R_f$ DNA derived from this selected subpopulation was used to generate the Phase II library (addition of variegated residues 31, 32, 34 and 39). The $1.8 \times 10^7$ independent transformants were obtained for each of the phase II libraries. The phase II libraries underwent three further rounds of binding and elution with the same target protease giving rise to the final selectants.

Following two phases of selection against human plasma kallikrein-agarose beads a number (10) of the final selection display-phage were sequenced. The amino-acid sequences are shown in Table 2, entries KBPcon1 through KKII/3190 C.

Table 23 shows that KkII/3(D) is a highly specific inhibitor of human Kallikrein. Phage that display the LACI-K1 derivative KkII/3(D) bind to Kallikrein beads at least 50-times more than it binds to other protease targets.

Preliminary measurements indicate that KKII/3#6 is a potent inhibitor of pKA with $K_i$ probably less than 500 pM.

Expression, Purification and Kinetic Analysis.

The three isolates KKII/3#6, KK2/#11, and KK2/#13 were recloned into a yeast expression vector. The yeast expression vector is derived from pMFalpha8 (KURJ82 and MIYA85). The LACI variant genes were fused to part of the matα 1 gene, generating a hybrid gene consisting of the matα 1 promoter-signal peptide and leader sequence-fused to the LACI variant. The cloning site is shown in Table 24. Note that the correctly processed LACI-K1 variant protein should be as detailed in Table 2 with the addition of residues glu-ala-ala-glu (SEQ ID NO: 70) to the N-terminal met (residue 1 in Table 2). Expression in *S. cerevisiae* gave acceptable yield typical of this system. Yeast-expressed LACI (kunitz domain 1), BPTI and LACI variants: KKII/3#6, KK2/#11, and KK2/#13 were purified by affinity chromatography using trypsin-agarose beads.

For larger-scale production, *Pichia pastoris* is a preferred host. The most preferred production system in *P. pastoris* is the alcohol oxidase system. Others have produced a number of proteins in the yeast *Pichia pastoris*. For example, Vedvick et al. (VEDV91) and Wagner et al. (WAGN92) produced aprotinin from the alcohol oxidase promoter with induction by methanol as a secreted protein in the culture medium at ≈1 mg/ml. Gregg et al. (GREG93) have reviewed production of a number of proteins in *P. pastoris*. Table 1 of GREG93 shows proteins that have been produced in *P. pastoris* and the yields.

All references, including those to U.S. and foreign patents or patent applications, and to nonpatent disclosures, are hereby incorporated by reference in their entirety.

TABLE 1

Sequence of whole LACI:

|   | 1   5 | 5 | 5 | 5 | 5 |
|---|---|---|---|---|---|
| 1 | MIYTMKKVHA | LWASVCLLLN | LAPAPLNAds | eedeehtiit | dtelpplklM |
| 51 | HSFCAFKADD | GPCKAIMKRF | FFNIFTRQCE | EFTYGGCEGN | QNRFESLEEC |
| 101 | KKMCTRDnan | riikttlqqee | kpdfcfleed | pgicrgyitr | yfynnqtkqd |
| 151 | erfkyggclg | nmnnfetlee | cknicedgpn | gfqvdnygtq | lnavnnsltp |
| 201 | qstkvpslfe | fhgpsweltp | adrglcrane | nrfyynsvig | kcrpfkysgc |
| 251 | ggnennftsk | qeclrackkg | fiqriskggl | iktkrkrkkq | rvkiayeeif |
| 301 | vknm | (SEQ ID NO. 18) | | | |

The signal sequence (1–28) is uppercase and underscored
LACI-K1 is uppercase
LACI-K2 is underscored
LACI-K3 is bold TABLE 2 is below.

TABLE 3

Summary of first selection of LACI-K1 domains for binding to pKA.

| BPTI # | (Lac I) | Library Residues | Preferred Residues |
|---|---|---|---|
| 13 | P | LHPR | HP |
| 16 | A | AG | AG |
| 17 | I | FYLHINA SCPRTVD G | NSA |
| 18 | M | all | HL |
| 19 | K | LWQMKAG SPRTVE | QLP |
| 31 | E | EQ | E |
| 32 | E | EQ | EQ |
| 34 | I | all | STI |
| 39 | E | all | GEA |

TABLE 2

Sequences of Kunitz domains, some of which inhibit human pKA.

Amino-acid sequence
```
                1111111111222222222233333333334444444444555555555
Ident  12345678901234567890123456789012345678901234567890123456778
```

| Ident | Amino-acid sequence | SEQ ID NO. |
|---|---|---|
| BPTI | RPDECLEPPYTGPCKARIIRYEYNAKAGLCQTFVYGGCRAKRNNEKSAEDCMRTCGGA | SEQ ID NO. 2 |
| LACI-K1 | mhsfcafkaddgpckaimkrfffniftrqceefiyggcegnqnrfesleeckkmctrd | SEQ ID NO. 3 |
| KBPcon1 | mhsfcafkaddgHckaNHQrfffniftrqcEEfSyggcGgnqnrfesleeckkmctrd | SEQ ID NO. 4 |
| KKII/3#1 | mhsfcafkaddgHckASLPrfffniftrqcEEflyggcEgnqnrfesleeckkmctrd | SEQ ID NO. 5 |
| KKII/3#2 | mhsfcafkaddgPckANHLrfffniftrqcEEfSyggcGgnqnrfesleeckkmctrd | SEQ ID NO. 6 |
| KKII/3#3 | mhsfcafkaddgHckANHQrfffniftrqcEEfIyggcGgnqnrfesleeckkmctrd | SEQ ID NO. 7 |
| KKII/3#4 | mhsfcafkaddgHckANHQrfffniftrqcEQfIyggcAgnqnrfesleeckkmctrd | SEQ ID NO. 8 |
| KKII/3#5 | mhsfcafkaddgHckASLPrfffniftrqcEEflyggcGgnqnrfesleeckkmctrd | SEQ ID NO. 9 |
| KKII/3#6 | mhsfcafkaddgHckANHQrfffniftrqcEEfSyggcGgnqnrfesleeckkmctrd | SEQ ID NO. 10 |
| KKII/3#7 | mhsfcafkaddgHckANHQrfffniftrqcEEfSyggcGgnqnrfesleeckkmctrd | SEQ ID NO. 11 |
| KKII/3#8 | mhsfcafkaddgHckANHQrfffniftrqcEEfSyggcGgnqnrfesleeckkmctrd | SEQ ID NO. 12 |
| KKII/3#9 | mhsfcafkaddgHckANHQrfffniftrqcEEfSyggcGgnqnrfesleeckkmctrd | SEQ ID NO. 13 |
| KKII/3#10 | mhsfcafkaddgHckGAHLrfffniftrqcEEflyggcEgnqnrfesleeckkmctrd | SEQ ID NO. 14 |
| KKI/3(a) | mhsfcafkaddgRckGAHLrfffniftrqceefiyggcegnqnrfesleeckkmctrd | SEQ ID NO. 15 |
| KKI/3(b) | mhsfcafkaddgPckAIHLrfffniftrqceefiyggcegnqnrfesleeckkmctrd | SEQ ID NO. 16 |
| KKI/3#C | mhsfcafkaddgHckANHQrfffniftrqcEEfSyggcGgnqnrfesleeckkmctrd | SEQ ID NO. 17 |
| KK2/#13 | mhsfcafkaDGgRcRGAHPrWffniftrqcEEfSyggcGgnqnrfesleeckkmctrd | SEQ ID NO. 19 |
| KK2/#14 | mhsfcafkaDGgRcRGAHPrWffniftrqcEEfSyggcGgnqnrfesleeckkmctrd | SEQ ID NO. 20 |
| KK2/#5 | mhsfcafkaDDgPcRAAHPrWffniftrqcEEfSyggcGgnqnrfesleeckkmctrd | SEQ ID NO. 21 |
| KK2/#11 | mhsfcafkaDDgPcRAAHPrWffniftrqcEEfSyggcGgnqnrfesleeckkmctrd | SEQ ID NO. 22 |
| KK2/#1 | mhsfcafkaDVgRcRGAHPrWffniftrqcEEfSyggcGgnqnrfesleeckkmctrd | SEQ ID NO. 23 |

TABLE 2-continued

Sequences of Kunitz domains, some of which inhibit human pKA.

```
                  Amino-acid sequence
                           1111111111222222222233333333334444444444555555555
           Ident   1234567890123456789012345678901234567890123456789012345678
```

| Ident | Amino-acid sequence | SEQ ID NO. |
|---|---|---|
| KK2/#4 | mhsfcafkaDVgRcRGAQPrFffniftrqcEEfSyggcGgnqnrfesleeckkmctrd | SEQ ID NO. 24 |
| KK2/#6 | mhsfcafkaDDgScRAAHLrWffniftrqcEEfSyggcGgnqnrfesleeckkmctrd | SEQ ID NO. 25 |
| KK2/#10 | mhsfcafkaEGgScRAAHQrWffniftrqcEEfSyggcGgnqnrfesleeckkmctrd | SEQ ID NO. 26 |
| KK2/#8 | mhsfcafkaDDgPcRGAHLrFffniftrqcEEfSyggcGgnqnrfesleeckkmctrd | SEQ ID NO. 27 |
| KK2/#3 | mhsfcafkaDDgHcRGALPrWffniftrqcEEfSyggcGgnqnrfesleeckkmctrd | SEQ ID NO. 28 |
| KK2/#9 | mhsfcafkaDSgNcRGNLPrFffniftrqcEEfSyggcGgnqnrfesleeckkmctrd | SEQ ID NO. 29 |
| KK2/#7 | mhsfcafkaDSgRcRGNHQrFffniftrqcEEfSyggcGgnqnrfesleeckkmctrd | SEQ ID NO. 30 |
| KK2/#12 | mhsfcafkaDGgRcRAIQPrWffniftrqcEEfSyggcGgnqnrfesleeckkmctrd | SEQ ID NO. 31 |
| KK2con1 | mhsfcafkaDDgRcRGAHPrWffniftrqcEEfSyggcGgnqnrfesleeckkmctrd | SEQ ID NO. 32 |
| Human LACI-K2 | KPDFCFLEEDPGICRGYITRYFYNNQTKQCERFKYGGCLGNMNNFETLEECKNICEDG | SEQ ID NO. 33 |
| DKI-1.2.1 | kpdfcfleedGgRcrgAHPrWfynnqtkqceEfSyggcGgnmnnfetleecknicedg | SEQ ID NO. 34 |
| Human LACI-K3 | GPSWCLTPADRGLCRANENRFYYNSVIGKCRPFKYSGCGGNENNFTSKQECLRACKKG | SEQ ID NO. 35 |
| DKI-1.3.1 | gpswcltpadDgPcraAHPrfyynsvigkcEpfSysgcggnennftskqeclrackkg | SEQ ID NO. 36 |
| Human collagen α3 KuDom | ETDICKLPKDEGRCRDFILKWYYDPNTKSCARFWYGGCGGNENKFGSQKECEKVCAPV | SEQ ID NO. 37 |
| DKI-2.1 | etdicklpkdegtcrAAHlkwyydpntkscaEfSyggcggnenkfgsqkecekvcapv | SEQ ID NO. 38 |
| TFPI-2 DOMAIN 1 | NAEICLLPLDYGPCRALLLRYYYDRYTQSCRQFLYGGCEGNANNFYTWEACDDACWRI | SEQ ID NO. 39 |
| DKI-3.1.1 | naeicllpldGgpcraAHlryyydrytqscEqfSyggcegnannfytweacddacwri | SEQ ID NO. 40 |
| tfpi-2 DOMAIN 2 | VPKVCRLQVS-VDDQCEGSTAKYFFNLSSMTCEKFFSGGCHRNR-IENRFPDEATCMGFCAPK | SEQ ID NO. 41 |
| DKI-3.2.1 | vpkvcrlqvs-vddqcRAAHPkyffnlssmtceEffsggchrnr-ienrfpdeatcmgfcapk | SEQ ID NO. 42 |
| TFPI-2 DOMAIN 3 | IPSFCYSPKDEGLCSANVTRYYFNPRYRTCDAFTYTGCGGNDNNFVSREDCKRACAKA | SEQ ID NO. 43 |
| DKI-3.3.1 | ipsfcyspkdegHcRaAHQryyfnpryrtcdaftytgcggndnnfvsredckracaka | SEQ ID NO. 44 |
| HUMAN ITI-K1 | KEDSCQLGYSAGPCMGMTSRYFYNGTSMACETFQYGGCMGNGNNFVTEKECLQTCRTV | SEQ ID NO. 45 |
| DKI-4.1.1 | kedscqlgyDagpcRgAHPryfyngtsmacetfSyggcGgngnnfvtekeclqtcrtv | SEQ ID NO. 46 |
| Human ITI-K2 | TVAACNLPIVRGPCRAFIQLWAFDAVKGKCVLFPYGGCQGNGNKFYSEKECREYCGVP | SEQ ID NO. 47 |
| DKI-4.2.1 | tvaacnlpiDDgpcraAHqlwafdavkgkcEEfSyggcEgngnkfysekecreycgvp | SEQ ID NO. 48 |
| DKI-4.2.2 | tvaacnlpiDDgpcraAHqRwafdavkgkcEEfSyggcqgngnkfysekecreycgvp | SEQ ID NO. 49 |
| HUMAN PROTEASE NEXIN-II | VREVCSEQAETGPCRAMISRWYFDVTEGKCAPFFYGGCGGNRNNFDTEEYCMAVCGSA | SEQ ID NO. 50 |
| DKI-5.1 | vrevcseqaetgpcraAHPrwyfdvtegkcEEfSyggcggnrnnfdteeycmavcgsa | SEQ ID NO. 51 |
| HKI B9 domain | LPNVCAFPMEKGPCQTYMTRWFFNFETGECELFAYGGCGGNSNNFLRKEKCEKFCKFT | SEQ ID NO. 53 |
| DKI-6.1 | lpnvcafpmeDgpcRAAHPrwffnfetgeceEfayggcggnsnnflrkekcekfckft | SEQ ID NO. 54 |
| DKI-7.1 | rpdfcleppEtgpcRaAHPryfynakaglcEEfvyggcGakrnnfksaedcmrtcgga | SEQ ID NO. 55 |

TABLE 8

Binding Data for Selected Kallikrein-binding Display-Phage.

| Display-Phage(a) | Fraction Bound(b) | Relative Binding(c) |
|---|---|---|
| LACI | $4.2 \times 10^{-6}$ | 1.0 |
| BPTI | $2.5 \times 10^{-5}$ | 6.0 |
| KKI/3(a) | $3.2 \times 10^{-3}$ | 761 |
| KKI/3(b) | $2.2 \times 10^{-3}$ | 524 |
| KKII/3#5 | $3.9 \times 10^{-3}$ | 928 |
| KKII/3#6 | $8.7 \times 10^{-3}$ | 2071 |

(a) Clonal isolates of display-phage. LACI-K1 is the parental molecule, BPTI (bovine pancreatic trypsin inhibitor) is a control and KKII/3 (5 and 6) and KKI/3 (a and b) were selected by binding to the target protease, kallikrein.
(b) The number of pfu's eluted after a binding experiment as a fraction of the input number ($10^{10}$ pfu's).
(c) Fraction bound relative to the parental display-phage, LACI-K1.

TABLE 9

Conservative and Semiconservative substitutions

| Initial AA type | Category | Conservative substitution | Semi-conservative substitution |
|---|---|---|---|
| A | Small non-polar or slightly polar | G, S, T | N, V, P, (C) |
| C | free SH disulfide | A, M, L, V, I nothing | F, G nothing |
| D | acidic, hydrophilic | E, N, S, T, Q | K, R, H, A |
| E | acidic, hydrophilic | D, Q, S, T, N | K, R, H, A |
| F | aromatic | W, Y, H, L, M | I, V, (C) |
| G | Gly-only conformation "normal" conformation | nothing A, S, N, T | nothing D, E, H, I, K, L, M, Q, R, V |
| H | amphoteric aromatic | Y, F, K, R | L, M, A, (C) |
| I | aliphatic, branched β carbon | V, L, M, A | F, Y, W, G (C) |
| K | basic | R, H | Q, N, S, T, D, E, A |
| L | aliphatic | M, I, V, A | F, Y, W, H, (C) |
| M | hydrophobic | L, I, V, A | Q, F, Y, W, (C), (R), (K), (E) |
| N | non-polar | S, T, (D), Q, | K, R |

TABLE 9-continued

Conservative and Semiconservative substitutions

| Initial AA type | Category | Conservative substitution | Semi-conservative substitution |
|---|---|---|---|
| | hydrophilic inflexible | A, G, (E) | |
| P | inflexible | V, I | A, (C), (D), (E), F, H, (K), L, M, N, Q, (R), S, T, W, Y |
| Q | aliphatic plus amide | N, E, A, S, T, D | M, L, K, R |
| R | basic | K, Q, H | S, T, E, D, A, |
| S | hydrophilic | A, T, G, N | D, E, R, K |
| T | hydrophilic | A, S, G, N, V | D, E, R, K, I |
| V | aliphatic, branched β carbon | I, L, M, A, T | P, (C) |
| W | aromatic | F, Y, H | L, M, I, V, (C) |
| Y | aromatic | F, W, H | L, M, I, V, (C) |

Changing from A, F, H, I, L, M, P, V, W, or Y to C is semiconservative if the new cysteine remains as a free thiol. Changing from M to E, R, K is semiconservative if the ionic tip of the new side group can reach the protein surface while the methylene groups make hydrophobic contacts.

Changing from P to one of K, R, E, or D is semiconservative if the side group is on or near the surface of the protein.

TABLE 14

Definition of a Kunitz Domain (SEQ ID NO. 52)

```
         1         2         3         4         5
12345678901234567890123456789012345678901234567890123456789012345678
xxxxCxxxxxGxCxxxxxxXXXxxxxxxCxxFxXXGCxXxxXxXxxxxxCxxxCxxx
```

Where:
X1, X2, X3, X4, X58, X57, and X56 may be absent,
X21 = Phe, Tyr, Trp,
X22 = Tyr or Phe,
X23 = Tyr or Phe,
X35 = Tyr or Trp,
X36 = Gly or Ser,
X40 = Gly or Ala,
X43 = Asn or Gly, and
X45 = Phe or Tyr

TABLE 15

Substitution to confer high affinity for pKA on KuDoms

| Position | Preferred | Allowed | Unlikely to work |
|---|---|---|---|
| 10 | Asp, Glu | Ala, Gly, Ser, Thr | Lys, Asn (Arg, Cys, Phe, His, Ile, Leu, Met, Pro, Gln, Val, Trp, Tyr) |
| 11 | Asp, Gly, Ser, Val | Glu, Leu, Met, [Asn, Ile, Ala, Thr] | (Cys, Phe, His, Lys, Pro, Gln, Arg, Trp, Tyr) |
| 12 | Gly | (Other amino acids ONLY if C$_{14}$—C$_{38}$ disulfide replaced by other amino acids.) | |
| 13 | Arg, His, Pro, Asn, Ser | [Thr, Ala, Gly, Lys, Gln] | Phe, Tyr, Cys, Leu, Ile, Val, Asp (Glu, Met, Trp) |
| 14 | Cys | (Other amino acids ONLY if C$_{38}$ also changed.) | |
| 15 | Arg, Lys | [Ala, Ser, Gly, Met, Asn, Gln] | (Cys, Asp, Glu, Phe, His, Ile, Leu, Pro, Thr, Val, Trp, Tyr) |

TABLE 15-continued

Substitution to confer high affinity for pKA on KuDoms

| Position | Preferred | Allowed | Unlikely to work |
|---|---|---|---|
| 16 | Ala, Gly | [Ser, Asp, Asn] | (Cys, Glu, Phe, His, Ile, Lys, Leu, Met, Pro, Gln, Arg, Thr, Val, Trp, Tyr) |
| 17 | Ala, Asn, Ser, Ile | [Gly, Val, Gln, Thr] | Cys, Asp, Phe, His, Pro, Arg, Tyr, (Glu, Lys, Met, Trp) |
| 18 | His, Leu, Gln | [Ala,] | Cys, Asp, Glu, Phe, Gly, Ile, Lys, Met, Asn, Pro, Arg, Ser, Thr, Val, Trp, Tyr |
| 19 | Pro, Gly, Leu | [Asn, Ile] | Ala, Glu, Gly, Met, Arg, Ser, Thr, Val, Trp, (Cys, Asp, Phe, His, Tyr) |
| 20 | Arg | Leu, Ala, Ser, Lys, Gln, Val | (Cys, Glu, Phe, Gly, His, Ile, Met, Asn, Pro, Thr, Trp, Tyr) |
| 21 | Trp, Phe | [Tyr, His, Ile] | Cys, Leu (Ala, Asp, Glu, Gly, Lys, Met, Asn, Pro, Gln, Arg, Ser, Thr, Val) |
| 31 | Glu | [Asp, Gln, Asn, Ser, Ala, Val, Leu, Ile, Thr] | (Arg, Lys, Cys, Phe, Gly, His, Met, Pro, Trp, Tyr) |
| 32 | Glu, Gln | [Asp, Asn, Pro, Thr, Leu, Ser, Ala, Gly, Val] | (Cys, Phe, His, Ile, Lys, Met, Arg, Trp, Tyr) |
| 33 | Phe | [Tyr] | other 18 excluded. |
| 34 | Ser, Thr, Ile | [Val, Ala, Asn, Gly, Leu] | Cys, Asp, Glu, Phe, His, Lys, Met, Pro, Gln, Arg, Trp, Tyr |
| 35 | Tyr | [Trp, Phe] | (other 17) |
| 36 | Gly | Ser, Ala | (other 17) |
| 37 | Gly | (Other amino-acid types allowed only if C$_{14}$—C$_{38}$ replaced by other types.) | |
| 38 | Cys | (Other amino acids ONLY if C$_{14}$ also changed.) | |
| 39 | Gly, Glu, Ala | [Ser, Asp] | Other 15. |

Under "Preferred", most highly preferred type are bold

Under "Allowed" are types not actually tested, but judged to be acceptable. Types shown in square brackets were allowed and not selected, but are so similar to types that were selected that the type is unlikely to abolish pKA binding. Such types are not preferred, but pKA-binding proteins could have such types.

Under "Unlikely to work", types shown outside parentheses have been tried and no isolates had that type; types in parentheses have not been tested, but are judged to be unsuitable from consideration of the types actually excluded.

TABLE 21

First Variegation of LACI-K1

```
 a  b  1  2  3  4  5  6  7  8  9 10
 A  E  M  H  S  F  C  A  F  K  A  D
lgcclgaglatglcatltcclttcltgclgcclttclaaglgctlgatl
    | NsiI |
```

TABLE 21-continued

First Variegation of LACI-K1

```
                        I IN
                        C IH
                    F IS F IY
                  Y IC L IS  L IS
                  L IP W IP  W IP
                  H IR Q IR  Q IR
                  I IT M IT  M IT
                    N IV K IV K IV
           L IP      A ID A IE A IE
    D G H IR C K A IG G D IG  G    R
    11 12 13 14 15 16 17 18  19   20
    lgatlggtlcNtltgtlaaalgStlNNtlNNSlNNglcgtl F F F N I F T R Q C
    21 22 23 24 25 26 27 28 29 30
    lttclttclttclaaclatclttclacglcgtlcagltgcl
                | MluI |

Q IE       N IH
              M IK       C II
              F IS       F IY
              Y IC       L IS
              L IP       W IP
              H IR       Q IR
              I IT       M IT
              N IV       K IV
              A ID       A IE
    E IQ E IQ  F G IW  Y  G  G  C G ID  G  N  Q
    31 32 33 34  35 36 37 38 39  40 41 42
    lSaglSaalttclNNSltaclggtlggtltgtlNNSlggtlaaclcagl
                                        | BstEII |

N R F E S L E E
              43 44 45 46 47 48 49 50
              laaclcggltt clgaaltctlct algaglgaal
                          | BstBI | | XbaI |
              | AgeI |
```

TABLE 21-continued

First Variegation of LACI-K1

```
    51 52 53 54 55 56 57 58 59 60
     C  K  K  M  C  T  R  D  G  A
    ltgtlaaglaaglatgltgclactlcgtlgaclggc gcc
                                | KasI |
```

The segment from NsiI to MluI gives 65,536 DNA sequences and 31,200 protein sequences. Second group of variegation gives 21,840 and 32,768 variants. This variegation can go in on a fragment having MluI and one of AgeI, BstBI, or XbaI ends. Because of the closeness between codon 42 and the 3restriction site, one will make a self-priming oligonucleotide, fill in, and cut with MluI and, for example, BstBI. Total variants are $2.726 \times 10^9$ and $8.59 \times 10^9$.

The DNA sequence has SEQ ID NO. 56.

The amino acid sequence has SEQ ID NO. 57.

TABLE 23

Specificity Results

| Protein displayed on M13 gIIIp | Immobilized enzyme tested | | | | |
|---|---|---|---|---|---|
| | Plasmin | Thrombin | pKA | Trypsin | Trypsin, 2 washes |
| LACI-K1 | 1 | 1 | 1 | 1 | 1 |
| KkII/3(D) | 3.4 | 1.5 | 196. | 2. | 1.4 |
| BPTI | 88. | 1.1 | 1.7 | 0.3 | .8 |

Numbers refer to relative binding of phage display clones compared to the parental phage display.

The KkII/3(D)(Kallikrein) clone retains the parental molecule's affinity for trypsin. KkII/3(D) was selected for binding to pKA.

TABLE 24

Mat α S. cerevisiae expression vectors:

Matα1 (Mfα8)
```
       K    R    P    R                SEQ ID NO. 58
5'-...IAAAIAGGICCTICGAIG...-3'         SEQ ID NO. 59
       | StuI |
              | XhoI |
```

Matα2 (after introduction of a linker into StuI-cut DNA)

```
                                            amino acids: SEQ ID NO. 60
    K    R    E    A    A    E    P    W    G    A .  .  L    E
5'IAAAIAGGIGAAIGCGIGCCIGAGICCAITGGIGGCIGCCITAAITAGICTCIGAGI3'
    | EagI |    | StyI |    | KasI |        | XhoI |
                                                DNA: SEQ ID NO. 61
```

Matα-LACI-K1, amino acids: SEQ ID NO. 62, DNA: SEQ ID NO. 63
```
    a    b    c    d    1  2  3  4  5  6  7  8
    K    R    E    A    A  E  M  H  S  F  C  A  F  K
5'IAAAIAGGIGAAIGCGIGCCIGAGIatglcatltcclttcltgclgctlttclaaal
    | EagI |    | | NsiI |
```

TABLE 24-continued

Mat α S. cerevisiae expression vectors:

```
 9 10 11    12 13  14 15 16 17 18 19 20
 A  D  D    G  P   C  K  A  I  M  K  R
lgctlgatlgaClggTlccGltgtlaaalgctlatclatglaaalcgtl
          |  RsrII  |         lBspHI l 21 22 23 24  25 26 27  28  29  30
 F  F  F  N   I  F  T   R   Q   C
lttclttclttclaaclattlttclacGlcgtlcagltgcl
                   |  MluI  |

31 32  33 34 35 36 37 38 39 40 41 42
 E  E   F  I  Y  G  G  C  E  G  N  Q
lgaglgaAlttClattltaclggtlggtltgtlgaalggtlaaclcagl
    |  EcoRI  |               |  BstEII  |

43 44   45 46  47 48  49 50
    N  R    F  E   S  L   E  E
laaclcgGlttclgaaltctlctAlgaglgaal
   |    | BstBI | | XbaI |
   |  AgeI  |

51 52  53 54 55 56 57 58 59 60
 C  K   K  M  C  T  R  D  G  A
ltgtlaaglaaglatgltgclactlcgtlgaclggclgccITAAITAGICTCIGAGI-3'
              |  KasI  |     |  XhoI  |
```

We expect that Matα pre sequence is cleaved before GLU$_a$—ALA$_b$—

TABLE 27

High specificity plasma Kallikrein inhibitors

LACI-K1 (SEQ ID NO. 3)
MHSFCAFKADDGPCKAIMKRFFFNIFTRQCEEFIYGGCEGNQNRFESLEECKKMCTRD
KKII/3#7 (SEQ ID NO. 11)
mhsfcafkaddgHckANHQrfffniftrqcEEfSyggcGgnqnrfesleeckkmctrd
KKII/3#7-K15A (SEQ ID NO. 64)
mhsfcafkaddghcAanhqrfffniftrqceefsyggcggnqnrfesleeckkmctrd
KK2/#13-R15A (SEQ ID NO. 65)
mhsfcafkaDGgRcAGAHPrWffniftrqcEEfSyggcGgnqnrfesleeckkmctrd
KK2/#11-R15S (SEQ ID NO. 66)
mhsfcafkaddgpcSaahprwffniftrqceefsyggcggnqnrfesleeckkmctrd

TABLE 49

| | Residue Number | | | | | | | | | | | |
|---|---|---|---|---|---|---|---|---|---|---|---|---|
| | 10 | 11 | 12 | 13 | 14 | 15 | 16 | 17 | 18 | 19 | 20 | 21 |
| LACI-K1 | D | D | G | P | C | K | A | I | M | K | R | F |
| Consensus of KKII/3 selectants | d | d | g | H | c | k | A | N | H | Q | r | f |
| KK Library #2 | NK DE | NI AD ST GV | g | FS YC LP HR IT NV AD G | c | KR | AG | NI AD ST GV | QL HP R | QL HP R | r | FW CL |
| KK2/#13 | — | G | — | — | — | — | — | — | — | — | — | — |
| KK2/#14 | — | G | — | — | — | — | — | — | — | — | — | — |
| KK2/#5 | — | — | — | P | — | — | A | — | — | — | — | — |
| KK2/#11 | — | — | — | P | — | — | A | — | — | — | — | — |
| KK2/#1 | — | V | — | — | — | — | — | — | — | — | — | — |
| KK2/#4 | — | V | — | — | — | — | — | — | Q | — | — | F |
| KK2/#6 | — | — | — | S | — | — | A | — | — | L | — | — |
| KK2/#10 | E | G | — | S | — | — | A | — | — | — | Q | — |

TABLE 49-continued

| | Residue Number | | | | | | | | | | |
|---|---|---|---|---|---|---|---|---|---|---|---|
| | 10 | 11 | 12 | 13 | 14 | 15 | 16 | 17 | 18 | 19 | 20 | 21 |
| KK2/#8 | — | — | — | P | — | — | — | — | — | L | — | F |
| KK2/#3 | — | — | — | H | — | — | — | — | L | — | — | — |
| KK2/#9 | — | S | — | N | — | — | — | N | L | — | — | F |
| KK2/#7 | — | S | — | — | — | — | — | N | — | Q | — | F |
| KK2/#12 | — | G | — | — | — | — | A | I | Q | — | — | — |
| Consensus #2 | D | D | g | R | c | R | G | A | H | P | r | W |

TABLE 750

DNA that embodies Library KKF.

```
                                        NIK
    M  H  S  F  C  A  F  K  A  DIE
    1  2  3  4  5  6  7  8  9  10
5'-cctcct atg cat tcc ttc tgc gcc ttc aag gct RaS
        | NsiI |

F IS
         Y IC
         L IH
         R II
I IV    V IT              V IT  (M) (K)
T IA    A IG              A IS  L IP  L IP
S IG    D IN              G ID  Q IR  R IH
D IN  G  P  C  KIR AIG I IN  H  Q  R
11    12 13 14 15  16   17   18 19 20
RNt ggt NNt tgt aRa gSt RNt cNS cNS cgt W IL
F IC F  F  N  I  F  T  R  (SEQ ID NO. 69)
21   22 23 24 25 26 27 28
tKS  ttc ttc aac atc ttc acg cgt tccctcc-3'  (SEQ ID NO. 67)
     3'-g ttg tag aag tgc gca agggagg-5'    (SEQ ID NO. 68)
                                    | MluI |
```

The RsrII and BspHI sites found in the parental LACI-K1 display gene (Table 6) are not present in Library KKF.

There are 1,536,000 amino-acid sequences and 4,194,304 DNA sequences. Met$_{18}$ and Lys$_{19}$ are not allowed in Library KKF.

Citations:
ADEL86: Adelman et al., *Blood* (1986) 68(6)1280–1284.
ALBR83a: Albrecht et al, *Hoppe-Seyler's Z Physiol Chem* (1983), 364:1697–1702.
ALBR83b: Albrecht et al., *Hoppe-Seyler's ZPhysiol Chem* (1983), 364:1703–1708.
ANBA88: Anba et al, *Biochimie* (1988) 70(6)727 –733.
ANGL87: Angliker et al., *Biochem J* (1987) 241(3)871–5.
AUER88: Auerswald et al., *Bio Chem Hoppe-Seyler* (1988), 369(Supplement):27–35.
BALD85: Balduyck et al., *Biol Chem Hoppe-Seyler* (1985) 366:9–14.
BANE90: Baneyx & Georgiou, *J Bacteriol* (1990) 172(1) 491–494.
BANE91: Baneyx & Georgiou, *J Bacteriol* (1991) 173(8) 2696–2703.
BERN93: Berndt et al., *Biochemistry* (1993) 32:4564–70.
BHOO92: Bhoola et al., *Pharmacological Reviews* (1992) 44(1)1–80.
BROW91: Browne et al., *GeneBank* entry M74220.
BROZ90: Broze et al., *Biochemistry* (1990) 29:7539–7546.
COLM87: Colman et al., Editors, Hemostasis and Thrombosis, Second Edition, 1987, J. B. Lippincott Company, Philadelphia, Pa.
COLM87a: Colman et al., Chapter 1 of COLM87.
DAVI79: Davis et al, U.S. Pat. No. 4,179,337 (1979).

DENN94a: Dennis & Lazarus, *J Biological Chem* (1994) 269:22129–22136.
DENN94b: Dennis & Lazarus, *J Biological Chem* (1994) 269:22137–22144.
EIGE90: Eigenbrot et al., *Protein Engineering* (1990), 3(7) 591–598.
ELLI92: Ellis et al., *Ann N Y Acad Sci* (1992) 667:13–3 1.
FIDL94: Fidler & Ellis, *Cell* (1994) 79:185–188.
FRAE89: Fraedrich et al., *Thorac Cardiovasc Surg* (1989) 37(2)89–91.
GARD93: Gardell, *Toxicol Pathol* (1993) 21(2)190–8.
GIRA89: Girard et al., *Nature* (1 989), 338:518–20.
GIRA91: Girard et al., *J BIOL. CHEM.* (1991) 266:5036–5041.
HOOV93: Hoover et al., *Biochemistry* (1993)32:1093643.
HORT91: Hortin & Trimpe, *J Biol Chem* (1991) 266(11) 6866–71.
HYNE90: Hynes et al., *Biochemistry* (1990), 29:10018–10022.
KEMP88b: Kemp & Bowen, *Tetrahedron Letts* (1988) 29:5077–5080.
KIDO88: Kido et al, *J Biol Chem* (1988), 263:18104–7.
KIDO90: Kido et al., *Biochem & Biophys Res Comm* (1990), 167(2)716–21.
KLIN91: Kline et al., *Biochem Biophys Res Commun* (1991) 177(3)1049–55.
LASK80: Laskowski & Kato, *Ann Rev Biochem* (1980), 49:593–626.
LEAT91: Leatherbarrow & Salacinski, *Biochemistry* (1991) 30(44)10717–21.
LOHM93: Lohrmann & J Marshall, *Refract Corneal Surg* (1993) 9(4)300–2.
LUCA83: Lucas et al., *J Biological Chem* (1983) 258(7) 4249–56.
MANN87: Mann & Foster, Chapter 10 of COLM87.
MARC85: Advanced Organic Chemistry, Third Edition March, J, John Wiley and Sons, New York, 1985; ISBN 0-471-88841-9.
MIYA85: Miyajima et al., *Gene* (1985) 37:155–161.
NEUH89: Neuhaus et al., *Lancet* (1989) 2(8668)924–5.
NOVO89: Novotny et al., *J. BIOL. CHEM.* (1989) 264:18832–18837.
PARK86: Park & Tulinsky, *Biochemistry* (1986) 25(14) 3977–3982.
PUTT89: Putternan, *Acta Chir Scand* (1989) 155(6–7)367.
ROBB87: Robbins, Chapter 21 of COLM87
SCHE67: Schechter & Berger, *Biochem Biophys Res Commun* (1967) 27:157–162.
SCHE68: Schechter & Berger, *Biochem Biophys Res Commun* (1968) 32:898–902.
SCHM87: Schmaier et al., Chapter 2 in COLM87.
SCHN86: Schnabel et al., *Biol Chem Hoppe-Seyler* (1986), 367:1167–76.
SHER89: Sheridan et al., *Dis Colon Rectum* (1989) 32(6) 505–8.

TIAN92: Tian et al., Int J Pept Protein Res (1992)40(2) 119–26.
VAND91: van der Logt et al, BIOCHEMISTRY (1991) 30:1571–1577.
VAND92: van Diji et al., EMBO J (1992) 11(8)2819–2828.
VARA83: Varadi & Patthy, Biochemistry (1983) 22:2440–2446.
VARA84: Varadi & Patthy, Biochemistry (1984) 23:2108–2112.
WILS93: Wilson et al., Tetrahedron (1993)49(17)3655–63.
WUNT88: Wun et al., J. BIOL. CHEM. (1988) 263:6001–6004.

We claim:

1. A kallikrein inhibiting protein which comprises a non-naturally naturally occurring Kunitz domain, wherein, at each of the residues of said domain corresponding to the below identified residues of BPTI, one of the following allowed amino acids is found:

| BPTI residue # | Allowed Amino Acid |
|---|---|
| 10 | Asp, Glu, Ala, Gly, Ser, Thr |
| 11 | Asp, Gly, Ser, Val, Glu, Leu, Met, Asn, Ile, Ala, Thr |
| 12 | Gly, and, if residue 14 or 38 is not Cys, any conservative or semi-conservative substitution for a "normal" conformation Gly as defined in Table 9 |
| 13 | Arg, His, Pro, Asn, Ser, Thr, Ala, Gly, Lys, Gln |
| 14 | Cys, and, if residue 38 is not Cys, any conservative or semi-conservative substitution for Cys |
| 15 | Arg, Lys, Ala, Ser, Gly, Met, Asn, Gln |
| 16 | Ala, Gly, Ser, Asp, Asn |
| 17 | Ala, Asn, Ser, Ile, Gly, Val, Gln, Thr |
| 18 | His, Leu, Gln, Ala |
| 19 | Pro, Gln, Leu, Asn, Ile |
| 20 | Arg, Leu, Ala, Ser, Lys, Gln, Val |
| 21 | Trp, Phe, Tyr, His, Ile |
| 31 | Glu, Asp, Gln, Asn, Ser, Ala, Val, Leu, Ile, Thr |
| 32 | Glu, Gln, Asp, Asn, Pro, Thr, |

| BPTI residue # | Allowed Amino Acid |
|---|---|
|  | Leu, Ser, Ala, Gly, Val |
| 33 | Phe, Tyr |
| 34 | Ser, Thr, Ile, Val, Ala, Asn, Gly, Leu |
| 35 | Tyr, Trp, Phe |
| 36 | Gly, Ser, Ala |
| 37 | Gly, and, if residue 14 or 38 is not Cys, any conservative or semi-conservative substitution for a "normal" conformation Gly as defined in Table 9 |
| 38 | Cys, and, if residue 14 is not Cys, any conservative or semi-conservative substitution for Cys |
| 39 | Gly, Glu, Ala, Ser, Asp. |

2. A method of treating a disorder attributable to excessive kallikrein activity which comprises administering, to a human or animal subject who would benefit therefrom, a kallikrein-inhibitory amount of the protein of claim 1.

3. A method of assaying for the presence of kallikrein in a sample which method comprises: providing the protein of claim 1 in labeled or insolubilized form, contacting said protein with said sample, and determining whether a complex of said protein and kallikrein in the sample is formed.

4. A method of purifying kallikrein from a mixture which comprises: providing the protein of claim 1 in insolubilized form, and contacting the mixture with said insolubilized protein so that kallikrein in the mixture is bound.

5. A kallikrein inhibiting protein which comprises a non-naturally occurring Kunitz domain, wherein, at each of the residues corresponding to the below identified residues, one of the following allowed amino acids is found:

| BPTI residue # | Allowed Amino Acid |
|---|---|
| 10 | Asp, Glu, Ala, Gly, Ser, Thr |
| 11 | Asp, Gly, Ser, Val, Glu, Leu, Met |
| 12 | Gly, and, if residue 14 or 38 is not Cys, or any conservative semi-conservative substitution for a "normal" conformation Gly as defined in Table 9 |
| 13 | Arg, His, Pro, Asn, Ser |
| 14 | Cys, and, if residue 38 is not Cys, any conservative or semi-conservative substitution for Cys |
| 15 | Arg, Lys |
| 16 | Ala, Gly |
| 17 | Ala, Asn, Ser, Ile |
| 18 | His, Leu, Gln |
| 19 | Pro, Gln, Leu |
| 20 | Arg, Leu, Ala, Ser, Lys, Gln, Val |
| 21 | Trp, Phe |
| 31 | Glu |
| 32 | Glu, Gln |
| 33 | Phe |
| 34 | Ser, Thr, Ile |
| 35 | Tyr |
| 36 | Gly, Ser, Ala |
| 37 | Gly, and, if residue 14 or 38 not Cys, any conservative or semi-conservative substitution for a "normal" conformation Gly as defined in Table 9 |

| BPTI residue # | Allowed Amino Acid |
|---|---|
| 38 | Cys, and, if residue corresponding to position 14 is not Cys, any conservative or semi-conservative substitution |
| 39 | Gly, Glu, Ala. |

6. The protein of claim 2 wherein, the Kunitz domain is further characterized as follows:

| BPTI Residue No. | Allowed Residue |
|---|---|
| 10 | Asp, Glu |
| 11 | Asp, Gly, Ser, Val |
| 12 | Gly |
| 14 | Cys |
| 20 | Arg |
| 36 | Gly |
| 37 | Gly |
| 38 | Cys. |

7. A method of preventing or treating a disorder attributable to excessive kallikrein activity which comprises administering, to a human or animal subject who would benefit therefrom, a kallikrein-inhibitory amount of the protein of claim 5.

8. A method of assaying for the presence of kallikrein in a sample which method comprises: providing the protein of claim 5 in labeled or insolubilized form, contacting said protein with said sample and determining whether a complex of said protein and kallikrein in the sample is formed.

9. A method of purifying kallikrein from a mixture which comprises: providing the protein of claim 5 in insolubilized form, and contacting the mixture with said insolubilized protein so that kallikrein in the mixture is bound.

10. A plasma kallikrein inhibiting protein which comprises a sequence that is homologous to a reference sequence being selected from the group consisting of: KKII/3#1 (SEQ ID NO. 5), KKII/3#2 (SEQ ID NO. 6), KKII/3#3 (SEQ ID NO. 7), KKII/3#4 (SEQ ID NO. 8), KKII/3#5 (SEQ ID NO. 9), KKII/3#6 (SEQ ID NO. 10), KKII/3#7 (SEQ ID NO. 11), KKII/3#8 (SEQ ID NO. 12), KKII/3#9 (SEQ ID NO. 13), KKII/3#10 (SEQ ID NO. 15), KK2/#11 (SEQ ID NO. 22), KK2/#13 (SEQ ID NO. 19), KK2/#1 (SEQ ID NO. 23), [KK2/#2, ] KK2/#3 (SEQ ID NO. 28), KK2/#4 (SEQ ID NO. 24), KK2/#6 (SEQ ID NO. 25), KK2/#7 (SEQ ID NO. 30), KK2/#8 (SEQ ID NO. 27), KK2/#9 (SEQ ID NO. 29) KK2/#10 (SEQ ID NO. 27), KK2/#12 (SEQ ID NO. 31), and KK2con1 (SEQ ID NO.32) as defined in Table 2.

11. A method of treating a disorder attributable to excessive kallikrein activity which comprises administering, to a human or animal subject who would benefit therefrom, a kallikrein-inhibitory amount of the protein of claim 10.

12. A method of assaying for the presence of kallikrein in a sample which method comprises: providing the protein of claim 10 in labeled or insolubilized form, contacting said protein with said sample, and determining whether a complex of said protein and kallikrein in the sample is formed.

13. A method of purifying kallikrein from a mixture which comprises: providing the protein of claim 10 in insolubilized form, and contacting the mixture with said insolubilized protein so that kallikrein in the mixture is bound.

* * * * *

UNITED STATES PATENT AND TRADEMARK OFFICE
CERTIFICATE OF CORRECTION

PATENT NO. : 5,795,865
DATED : August 18, 1998
INVENTOR(S) : Markland et al.

It is certified that error appears in the above-identified patent and that said Letters Patent is hereby corrected as shown below:

On the title page, item [75] Inventors: "Willaim" should read --William--.

Column 1, line 52, after "Genebank entry" insert --P03952--.
Column 2, line 64, after "from a" delete --.-- {period}.
Column 3, line 14, "the" should read --they--.
Column 4, line 55, "purposed" should read --purposes--.
Column 5, line 56, "S 1" should read --S1--.
Column 6, line 20, delete "]".
Column 7, line 21, "screeneing" should read --screening--; line 24 "K" should read --$K_i$--.
Column 8, line 24, "D 16G" should read --D16G--; line 35, "S 17A" should read --S17A--;
    line 35 "T18H,E19P" should read --T18H, E19P--.
    line 41, "S 15R" should read --S15R--; line 60, "A3 1E" should read --A31E--.
Column 9, line 3, "RI18H" should read --I18H--; line 7, "RI18H" should read --I18H--;
    line 8, "MODIFICARION" should read --MODIFICATION--;
    line 29, "$R_{,15}$" should read --$R_{15}$--; line 53, after "sequences" insert --.-- {period}.

UNITED STATES PATENT AND TRADEMARK OFFICE
CERTIFICATE OF CORRECTION

PATENT NO. : 5,795,865
DATED : August 18, 1998
INVENTOR(S) : Marland et al.

It is certified that error appears in the above-identified patent and that said Letters Patent is hereby corrected as shown below:

Column 11, line 23, after "small and" delete "the".
Column 14, line 56, "optimiize" should read --optimize--.
Column 15, line 31, "($F^{-)}$" should read --($F^-$)--.
Column 71, line 51, after "non-naturally" delete "naturally".
Column 73, line 44, delete "or" before "any conservative", and insert --or-- after "conservative".
Column 74, line 8, after "substitution" insert --for Cys--; line 25, delete "preventing or";
      line 33, after "said sample" insert --,-- *{comma}*; line 48, delete "[KK2/#2, ]".

Signed and Sealed this

Ninth Day of March, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH:8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ile Val Gly Gly Thr Asn Ser Ser
 1               5
```

( 2 ) INFORMATION FOR SEQ ID NO:2:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Arg Pro Asp Phe Cys Leu Glu Pro Pro Tyr Thr Gly Pro Cys Lys Ala
 1               5                  10                  15
Arg Ile Ile Arg Tyr Phe Tyr Asn Ala Lys Ala Gly Leu Cys Gln Thr
                20                  25                  30
Phe Val Tyr Gly Gly Cys Arg Ala Lys Arg Asn Asn Phe Lys Ser Ala
                35                  40                  45
Glu Asp Cys Met Arg Thr Cys Gly Gly Ala
                50                  55
```

( 2 ) INFORMATION FOR SEQ ID NO:3:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met His Ser Phe Cys Ala Phe Lys Ala Asp Asp Gly Pro Cys Lys Ala
 1               5                  10                  15
Ile Met Lys Arg Phe Phe Phe Asn Ile Phe Thr Arg Gln Cys Glu Glu
                20                  25                  30
Phe Ile Tyr Gly Gly Cys Glu Gly Asn Gln Asn Arg Phe Glu Ser Leu
                35                  40                  45
```

```
Glu Glu Cys Lys Lys Met Cys Thr Arg Asp
    50                  55
```

( 2 ) INFORMATION FOR SEQ ID NO:4:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met His Ser Phe Cys Ala Phe Lys Ala Asp Asp Gly His Cys Lys Ala
  1           5                   10                  15
Asn His Gln Arg Phe Phe Phe Asn Ile Phe Thr Arg Gln Cys Glu Glu
             20                  25                  30
Phe Ser Tyr Gly Gly Cys Gly Gly Asn Gln Asn Arg Phe Glu Ser Leu
             35              40                  45
Glu Glu Cys Lys Lys Met Cys Thr Arg Asp
    50                  55
```

( 2 ) INFORMATION FOR SEQ ID NO:5:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Met His Ser Phe Cys Ala Phe Lys Ala Asp Asp Gly His Cys Lys Ala
  1           5                   10                  15
Ser Leu Pro Arg Phe Phe Phe Asn Ile Phe Thr Arg Gln Cys Glu Glu
             20                  25                  30
Phe Ile Tyr Gly Gly Cys Glu Gly Asn Gln Asn Arg Phe Glu Ser Leu
             35              40                  45
Glu Glu Cys Lys Lys Met Cys Thr Arg Asp
    50                  55
```

( 2 ) INFORMATION FOR SEQ ID NO:6:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met His Ser Phe Cys Ala Phe Lys Ala Asp Asp Gly Pro Cys Lys Ala
  1           5                   10                  15
Asn His Leu Arg Phe Phe Phe Asn Ile Phe Thr Arg Gln Cys Glu Glu
             20                  25                  30
Phe Ser Tyr Gly Gly Cys Gly Gly Asn Gln Asn Arg Phe Glu Ser Leu
             35              40                  45
Glu Glu Cys Lys Lys Met Cys Thr Arg Asp
    50                  55
```

( 2 ) INFORMATION FOR SEQ ID NO:7:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:7:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                      45

Glu Glu Cys Lys Lys Met Cys Thr Arg Asp
    50                  55

( 2 ) INFORMATION FOR SEQ ID NO:8:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                      45

Glu Glu Cys Lys Lys Met Cys Thr Arg Asp
    50                  55

( 2 ) INFORMATION FOR SEQ ID NO:9:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
        35                  40                      45

Glu Glu Cys Lys Lys Met Cys Thr Arg Asp
    50                  55

( 2 ) INFORMATION FOR SEQ ID NO:10:

( i ) SEQUENCE CHARACTERISTICS:
( A ) LENGTH: 58 amino acids
( B ) TYPE: amino acid
( C ) STRANDEDNESS: single (D) TOPOLOGY: linear (ii) MOLECULE TYPE: protein (xi) SEQUENCE DESCRIPTION: SEQ ID NO:10:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

(2) INFORMATION FOR SEQ ID NO:11:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:11:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

(2) INFORMATION FOR SEQ ID NO:12:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:12:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

(2) INFORMATION FOR SEQ ID NO:13:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:13:

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:14:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met His Ser Phe Cys Ala Phe Lys Ala Asp Asp Gly His Cys Lys Gly
1               5                   10                  15

Ala His Leu Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:15:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Met His Ser Phe Cys Ala Phe Lys Ala Asp Asp Gly Arg Cys Lys Gly
1               5                   10                  15

Ala His Leu Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:16:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Met His Ser Phe Cys Ala Phe Lys Ala Asp Asp Gly Pro Cys Lys Ala
1               5                   10                  15

Ile His Leu Arg Phe Phe Phe Asn Ile Phe Thr Arg Gln Cys Glu Glu

|  | 20 |  |  |  |  | 25 |  |  |  |  | 30 |  |  |
|---|---|---|---|---|---|---|---|---|---|---|---|---|---|
| Phe | Ile | Tyr | Gly | Gly | Cys | Glu | Gly | Asn | Gln | Asn | Arg | Phe | Glu | Ser | Leu |
|  |  | 35 |  |  |  |  | 40 |  |  |  |  | 45 |  |  |

| Glu | Glu | Cys | Lys | Lys | Met | Cys | Thr | Arg | Asp |
|---|---|---|---|---|---|---|---|---|---|
|  | 50 |  |  |  |  | 55 |  |  |  |

( 2 ) INFORMATION FOR SEQ ID NO:17:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

| Met | His | Ser | Phe | Cys | Ala | Phe | Lys | Ala | Asp | Asp | Gly | His | Cys | Lys | Ala |
|---|---|---|---|---|---|---|---|---|---|---|---|---|---|---|---|
| 1 |  |  |  | 5 |  |  |  |  | 10 |  |  |  |  | 15 |  |

| Asn | His | Gln | Arg | Phe | Phe | Phe | Asn | Ile | Phe | Thr | Arg | Gln | Cys | Glu | Glu |
|---|---|---|---|---|---|---|---|---|---|---|---|---|---|---|---|
|  |  |  | 20 |  |  |  |  | 25 |  |  |  |  | 30 |  |  |

| Phe | Ser | Tyr | Gly | Gly | Cys | Gly | Gly | Asn | Gln | Asn | Arg | Phe | Glu | Ser | Leu |
|---|---|---|---|---|---|---|---|---|---|---|---|---|---|---|---|
|  |  | 35 |  |  |  |  | 40 |  |  |  |  | 45 |  |  |  |

| Glu | Glu | Cys | Lys | Lys | Met | Cys | Thr | Arg | Asp |
|---|---|---|---|---|---|---|---|---|---|
|  | 50 |  |  |  |  | 55 |  |  |  |

( 2 ) INFORMATION FOR SEQ ID NO:18:

( i ) SEQUENCE CHARACTERISTICS:
        ( A ) LENGTH:304 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

| Met | Ile | Tyr | Thr | Met | Lys | Lys | Val | His | Ala | Leu | Trp | Ala | Ser | Val | Cys |
|---|---|---|---|---|---|---|---|---|---|---|---|---|---|---|---|
| 1 |  |  |  | 5 |  |  |  |  | 10 |  |  |  |  | 15 |  |

| Leu | Leu | Leu | Asn | Leu | Ala | Pro | Ala | Pro | Leu | Asn | Ala | Asp | Ser | Glu | Glu |
|---|---|---|---|---|---|---|---|---|---|---|---|---|---|---|---|
|  |  |  | 20 |  |  |  |  | 25 |  |  |  |  | 30 |  |  |

| Asp | Glu | Glu | His | Thr | Ile | Ile | Thr | Asp | Thr | Glu | Leu | Pro | Pro | Leu | Lys |
|---|---|---|---|---|---|---|---|---|---|---|---|---|---|---|---|
|  |  | 35 |  |  |  |  | 40 |  |  |  |  | 45 |  |  |  |

| Leu | Met | His | Ser | Phe | Cys | Ala | Phe | Lys | Ala | Asp | Asp | Gly | Pro | Cys | Lys |
|---|---|---|---|---|---|---|---|---|---|---|---|---|---|---|---|
|  | 50 |  |  |  |  | 55 |  |  |  |  | 60 |  |  |  |  |

| Ala | Ile | Met | Lys | Arg | Phe | Phe | Asn | Ile | Phe | Thr | Arg | Gln | Cys | Glu |
|---|---|---|---|---|---|---|---|---|---|---|---|---|---|---|
| 65 |  |  |  |  | 70 |  |  |  |  | 75 |  |  |  |  | 80 |

| Glu | Phe | Ile | Tyr | Gly | Gly | Cys | Glu | Gly | Asn | Gln | Asn | Arg | Phe | Glu | Ser |
|---|---|---|---|---|---|---|---|---|---|---|---|---|---|---|---|
|  |  |  |  | 85 |  |  |  |  | 90 |  |  |  |  | 95 |  |

| Leu | Glu | Glu | Cys | Lys | Lys | Met | Cys | Thr | Arg | Asp | Asn | Ala | Asn | Arg | Ile |
|---|---|---|---|---|---|---|---|---|---|---|---|---|---|---|---|
|  |  |  | 100 |  |  |  |  | 105 |  |  |  |  | 110 |  |  |

| Ile | Lys | Thr | Thr | Leu | Gln | Gln | Glu | Lys | Pro | Asp | Phe | Cys | Phe | Leu | Glu |
|---|---|---|---|---|---|---|---|---|---|---|---|---|---|---|---|
|  |  | 115 |  |  |  |  | 120 |  |  |  |  | 125 |  |  |  |

| Glu | Asp | Pro | Gly | Ile | Cys | Arg | Gly | Tyr | Ile | Thr | Arg | Tyr | Phe | Tyr | Asn |
|---|---|---|---|---|---|---|---|---|---|---|---|---|---|---|---|
|  | 130 |  |  |  |  | 135 |  |  |  |  | 140 |  |  |  |  |

| Asn | Gln | Thr | Lys | Gln | Cys | Glu | Arg | Phe | Lys | Tyr | Gly | Gly | Cys | Leu | Gly |
|---|---|---|---|---|---|---|---|---|---|---|---|---|---|---|---|
| 145 |  |  |  |  | 150 |  |  |  |  | 155 |  |  |  |  | 160 |

| Asn | Met | Asn | Asn | Phe | Glu | Thr | Leu | Glu | Glu | Cys | Lys | Asn | Ile | Cys | Glu |
|---|---|---|---|---|---|---|---|---|---|---|---|---|---|---|---|
|  |  |  |  | 165 |  |  |  |  | 170 |  |  |  |  | 175 |  |

| Asp | Gly | Pro | Asn | Gly | Phe | Gln | Val | Asp | Asn | Tyr | Gly | Thr | Gln | Leu | Asn |
|---|---|---|---|---|---|---|---|---|---|---|---|---|---|---|---|

|     |     |     | 180 |     |     |     |     | 185 |     |     |     |     | 190 |     |     |
| --- | --- | --- | --- | --- | --- | --- | --- | --- | --- | --- | --- | --- | --- | --- | --- |
| Ala | Val | Asn | Asn | Ser | Leu | Thr | Pro | Gln | Ser | Thr | Lys | Val | Pro | Ser | Leu |
|     |     | 195 |     |     |     |     | 200 |     |     |     | 205 |     |     |     |     |
| Phe | Glu | Phe | His | Gly | Pro | Ser | Trp | Cys | Leu | Thr | Pro | Ala | Asp | Arg | Gly |
|     | 210 |     |     |     |     | 215 |     |     |     |     | 220 |     |     |     |     |
| Leu | Cys | Arg | Ala | Asn | Glu | Asn | Arg | Phe | Tyr | Tyr | Asn | Ser | Val | Ile | Gly |
| 225 |     |     |     |     | 230 |     |     |     |     | 235 |     |     |     |     | 240 |
| Lys | Cys | Arg | Pro | Phe | Lys | Tyr | Ser | Gly | Cys | Gly | Gly | Asn | Glu | Asn | Asn |
|     |     |     |     | 245 |     |     |     |     | 250 |     |     |     |     | 255 |     |
| Phe | Thr | Ser | Lys | Gln | Glu | Cys | Leu | Arg | Ala | Cys | Lys | Lys | Gly | Phe | Ile |
|     |     |     | 260 |     |     |     |     | 265 |     |     |     |     | 270 |     |     |
| Gln | Arg | Ile | Ser | Lys | Gly | Gly | Leu | Ile | Lys | Thr | Lys | Arg | Lys | Arg | Lys |
|     |     | 275 |     |     |     |     | 280 |     |     |     |     | 285 |     |     |     |
| Lys | Gln | Arg | Val | Lys | Ile | Ala | Tyr | Glu | Glu | Ile | Phe | Val | Lys | Asn | Met |
|     | 290 |     |     |     | 295 |     |     |     |     | 300 |     |     |     |     |     |

( 2 ) INFORMATION FOR SEQ ID NO:19:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

| Met | His | Ser | Phe | Cys | Ala | Phe | Lys | Ala | Asp | Gly | Gly | Arg | Cys | Arg | Gly |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ala | His | Pro | Arg | Trp | Phe | Phe | Asn | Ile | Phe | Thr | Arg | Gln | Cys | Glu | Glu |
|     |     |     | 20 |     |     |     |     | 25 |     |     |     |     | 30 |     |     |
| Phe | Ser | Tyr | Gly | Gly | Cys | Gly | Gly | Asn | Gln | Asn | Arg | Phe | Glu | Ser | Leu |
|     |     |     | 35 |     |     |     | 40 |     |     |     |     | 45 |     |     |     |
| Glu | Glu | Cys | Lys | Lys | Met | Cys | Thr | Arg | Asp |     |     |     |     |     |     |
|     | 50 |     |     |     |     | 55 |     |     |     |     |     |     |     |     |     |

( 2 ) INFORMATION FOR SEQ ID NO:20:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

| Met | His | Ser | Phe | Cys | Ala | Phe | Lys | Ala | Asp | Gly | Gly | Arg | Cys | Arg | Gly |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ala | His | Pro | Arg | Trp | Phe | Phe | Asn | Ile | Phe | Thr | Arg | Gln | Cys | Glu | Glu |
|     |     |     | 20 |     |     |     |     | 25 |     |     |     |     | 30 |     |     |
| Phe | Ser | Tyr | Gly | Gly | Cys | Gly | Gly | Asn | Gln | Asn | Arg | Phe | Glu | Ser | Leu |
|     |     |     | 35 |     |     |     | 40 |     |     |     |     | 45 |     |     |     |
| Glu | Glu | Cys | Lys | Lys | Met | Cys | Thr | Arg | Asp |     |     |     |     |     |     |
|     | 50 |     |     |     |     | 55 |     |     |     |     |     |     |     |     |     |

( 2 ) INFORMATION FOR SEQ ID NO:21:

( i ) SEQUENCE CHARACTERISTICS:
        ( A ) LENGTH:58 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:21:

| Met | His | Ser | Phe | Cys | Ala | Phe | Lys | Ala | Asp | Asp | Gly | Pro | Cys | Arg | Ala |
|---|---|---|---|---|---|---|---|---|---|---|---|---|---|---|---|
| 1 | | | | 5 | | | | | 10 | | | | | 15 | |

| Ala | His | Pro | Arg | Trp | Phe | Phe | Asn | Ile | Phe | Thr | Arg | Gln | Cys | Glu | Glu |
|---|---|---|---|---|---|---|---|---|---|---|---|---|---|---|---|
| | | | 20 | | | | | 25 | | | | | 30 | | |

| Phe | Ser | Tyr | Gly | Gly | Cys | Gly | Gly | Asn | Gln | Asn | Arg | Phe | Glu | Ser | Leu |
|---|---|---|---|---|---|---|---|---|---|---|---|---|---|---|---|
| | | 35 | | | | | 40 | | | | | 45 | | | |

| Glu | Glu | Cys | Lys | Lys | Met | Cys | Thr | Arg | Asp |
|---|---|---|---|---|---|---|---|---|---|
| | 50 | | | | | 55 | | | |

( 2 ) INFORMATION FOR SEQ ID NO:22:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

| Met | His | Ser | Phe | Cys | Ala | Phe | Lys | Ala | Asp | Asp | Gly | Pro | Cys | Arg | Ala |
|---|---|---|---|---|---|---|---|---|---|---|---|---|---|---|---|
| 1 | | | | 5 | | | | | 10 | | | | | 15 | |

| Ala | His | Pro | Arg | Trp | Phe | Phe | Asn | Ile | Phe | Thr | Arg | Gln | Cys | Glu | Glu |
|---|---|---|---|---|---|---|---|---|---|---|---|---|---|---|---|
| | | | 20 | | | | | 25 | | | | | 30 | | |

| Phe | Ser | Tyr | Gly | Gly | Cys | Gly | Gly | Asn | Gln | Asn | Arg | Phe | Glu | Ser | Leu |
|---|---|---|---|---|---|---|---|---|---|---|---|---|---|---|---|
| | | 35 | | | | | 40 | | | | | 45 | | | |

| Glu | Glu | Cys | Lys | Lys | Met | Cys | Thr | Arg | Asp |
|---|---|---|---|---|---|---|---|---|---|
| | 50 | | | | | 55 | | | |

( 2 ) INFORMATION FOR SEQ ID NO:23:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

| Met | His | Ser | Phe | Cys | Ala | Phe | Lys | Ala | Asp | Val | Gly | Arg | Cys | Arg | Gly |
|---|---|---|---|---|---|---|---|---|---|---|---|---|---|---|---|
| 1 | | | | 5 | | | | | 10 | | | | | 15 | |

| Ala | His | Pro | Arg | Trp | Phe | Phe | Asn | Ile | Phe | Thr | Arg | Gln | Cys | Glu | Glu |
|---|---|---|---|---|---|---|---|---|---|---|---|---|---|---|---|
| | | | 20 | | | | | 25 | | | | | 30 | | |

| Phe | Ser | Tyr | Gly | Gly | Cys | Gly | Gly | Asn | Gln | Asn | Arg | Phe | Glu | Ser | Leu |
|---|---|---|---|---|---|---|---|---|---|---|---|---|---|---|---|
| | | 35 | | | | | 40 | | | | | 45 | | | |

| Glu | Glu | Cys | Lys | Lys | Met | Cys | Thr | Arg | Asp |
|---|---|---|---|---|---|---|---|---|---|
| | 50 | | | | | 55 | | | |

( 2 ) INFORMATION FOR SEQ ID NO:24:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

Met His Ser Phe Cys Ala Phe Lys Ala Asp Val Gly Arg Cys Arg Gly
1               5                   10                  15

Ala Gln Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

( 2 ) INFORMATION FOR SEQ ID NO:25:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

( 2 ) INFORMATION FOR SEQ ID NO:26:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

Met His Ser Phe Cys Ala Phe Lys Ala Glu Gly Gly Ser Cys Arg Ala
1               5                   10                  15

Ala His Gln Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50              55

( 2 ) INFORMATION FOR SEQ ID NO:27:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

Met His Ser Phe Cys Ala Phe Lys Ala Asp Asp Gly Pro Cys Arg Gly
1               5                   10                  15

Ala His Leu Arg Phe Phe Phe Asn Ile Phe Thr Arg Gln Cys Glu Glu

|  |  | 20 |  |  |  | 25 |  |  |  |  | 30 |  |  |
|---|---|---|---|---|---|---|---|---|---|---|---|---|---|

Phe Ser Tyr Gly Gly Cys Gly Gly Asn Gln Asn Arg Phe Glu Ser Leu
          35                    40                45

Glu Glu Cys Lys Lys Met Cys Thr Arg Asp
50                      55

(2) INFORMATION FOR SEQ ID NO:28:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Met His Ser Phe Cys Ala Phe Lys Ala Asp Asp Gly His Cys Arg Gly
1               5                   10                  15

Ala Leu Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                      55

(2) INFORMATION FOR SEQ ID NO:29:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Met His Ser Phe Cys Ala Phe Lys Ala Asp Ser Gly Asn Cys Arg Gly
1               5                   10                  15

Asn Leu Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                      55

(2) INFORMATION FOR SEQ ID NO:30:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Met His Ser Phe Cys Ala Phe Lys Ala Asp Ser Gly Arg Cys Arg Gly
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

```
Glu Glu Cys Lys Lys Met Cys Thr Arg Asp
50                  55
```

( 2 ) INFORMATION FOR SEQ ID NO:31:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

```
Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                  55
```

( 2 ) INFORMATION FOR SEQ ID NO:32:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                  55
```

( 2 ) INFORMATION FOR SEQ ID NO:33:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

```
Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
                20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly
50                  55
```

( 2 ) INFORMATION FOR SEQ ID NO:34:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:34:

| Lys | Pro | Asp | Phe | Cys | Phe | Leu | Glu | Glu | Asp | Gly | Gly | Arg | Cys | Arg | Gly |
|---|---|---|---|---|---|---|---|---|---|---|---|---|---|---|---|
| 1 | | | | 5 | | | | | 10 | | | | | 15 | |
| Ala | His | Pro | Arg | Trp | Phe | Tyr | Asn | Asn | Gln | Thr | Lys | Gln | Cys | Glu | Glu |
| | | | 20 | | | | | 25 | | | | | 30 | | |
| Phe | Ser | Tyr | Gly | Gly | Cys | Gly | Gly | Asn | Met | Asn | Asn | Phe | Glu | Thr | Leu |
| | | 35 | | | | | 40 | | | | | 45 | | | |
| Glu | Glu | Cys | Lys | Asn | Ile | Cys | Glu | Asp | Gly | | | | | | |
| 50 | | | | | 55 | | | | | | | | | | |

( 2 ) INFORMATION FOR SEQ ID NO:35:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:35:

| Gly | Pro | Ser | Trp | Cys | Leu | Thr | Pro | Ala | Asp | Arg | Gly | Leu | Cys | Arg | Ala |
|---|---|---|---|---|---|---|---|---|---|---|---|---|---|---|---|
| 1 | | | | 5 | | | | | 10 | | | | | 15 | |
| Asn | Glu | Asn | Arg | Phe | Tyr | Tyr | Asn | Ser | Val | Ile | Gly | Lys | Cys | Arg | Pro |
| | | | 20 | | | | | 25 | | | | | 30 | | |
| Phe | Lys | Tyr | Ser | Gly | Cys | Gly | Gly | Asn | Glu | Asn | Asn | Phe | Thr | Ser | Lys |
| | | 35 | | | | | 40 | | | | | 45 | | | |
| Gln | Glu | Cys | Leu | Arg | Ala | Cys | Lys | Lys | Gly | | | | | | |
| 50 | | | | | 55 | | | | | | | | | | |

( 2 ) INFORMATION FOR SEQ ID NO:36:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:36:

| Gly | Pro | Ser | Trp | Cys | Leu | Thr | Pro | Ala | Asp | Asp | Gly | Pro | Cys | Arg | Ala |
|---|---|---|---|---|---|---|---|---|---|---|---|---|---|---|---|
| 1 | | | | 5 | | | | | 10 | | | | | 15 | |
| Ala | His | Pro | Arg | Phe | Tyr | Tyr | Asn | Ser | Val | Ile | Gly | Lys | Cys | Glu | Pro |
| | | | 20 | | | | | 25 | | | | | 30 | | |
| Phe | Ser | Tyr | Ser | Gly | Cys | Gly | Gly | Asn | Glu | Asn | Asn | Phe | Thr | Ser | Lys |
| | | 35 | | | | | 40 | | | | | 45 | | | |
| Gln | Glu | Cys | Leu | Arg | Ala | Cys | Lys | Lys | Gly | | | | | | |
| 50 | | | | | 55 | | | | | | | | | | |

( 2 ) INFORMATION FOR SEQ ID NO:37:

( i ) SEQUENCE CHARACTERISTICS:
  ( A ) LENGTH: 58 amino acids
  ( B ) TYPE: amino acid
  ( C ) STRANDEDNESS: single (D) TOPOLOGY: linear (ii) MOLECULE TYPE: protein (xi) SEQUENCE DESCRIPTION: SEQ ID NO:37:

| Glu | Thr | Asp | Ile | Cys | Lys | Leu | Pro | Lys | Asp | Glu | Gly | Thr | Cys | Arg | Asp |
|---|---|---|---|---|---|---|---|---|---|---|---|---|---|---|---|
| 1 | | | | 5 | | | | | 10 | | | | | 15 | |

| Phe | Ile | Leu | Lys | Trp | Tyr | Tyr | Asp | Pro | Asn | Thr | Lys | Ser | Cys | Ala | Arg |
|---|---|---|---|---|---|---|---|---|---|---|---|---|---|---|---|
| | | | 20 | | | | | 25 | | | | | 30 | | |

| Phe | Trp | Tyr | Gly | Gly | Cys | Gly | Gly | Asn | Glu | Asn | Lys | Phe | Gly | Ser | Gln |
|---|---|---|---|---|---|---|---|---|---|---|---|---|---|---|---|
| | | 35 | | | | | 40 | | | | | 45 | | | |

| Lys | Glu | Cys | Glu | Lys | Val | Cys | Ala | Pro | Val |
|---|---|---|---|---|---|---|---|---|---|
| | 50 | | | | | 55 | | | |

(2) INFORMATION FOR SEQ ID NO:38:

(i) SEQUENCE CHARACTERISTICS:
      (A) LENGTH:58 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:38:

| Glu | Thr | Asp | Ile | Cys | Lys | Leu | Pro | Lys | Asp | Glu | Gly | Thr | Cys | Arg | Ala |
|---|---|---|---|---|---|---|---|---|---|---|---|---|---|---|---|
| 1 | | | | 5 | | | | | 10 | | | | | 15 | |

| Ala | His | Leu | Lys | Trp | Tyr | Tyr | Asp | Pro | Asn | Thr | Lys | Ser | Cys | Ala | Glu |
|---|---|---|---|---|---|---|---|---|---|---|---|---|---|---|---|
| | | | 20 | | | | | 25 | | | | | 30 | | |

| Phe | Ser | Tyr | Gly | Gly | Cys | Gly | Gly | Asn | Glu | Asn | Lys | Phe | Gly | Ser | Gln |
|---|---|---|---|---|---|---|---|---|---|---|---|---|---|---|---|
| | | 35 | | | | | 40 | | | | | 45 | | | |

| Lys | Glu | Cys | Glu | Lys | Val | Cys | Ala | Pro | Val |
|---|---|---|---|---|---|---|---|---|---|
| | 50 | | | | | 55 | | | |

(2) INFORMATION FOR SEQ ID NO:39:

(i) SEQUENCE CHARACTERISTICS:
      (A) LENGTH:58 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:39:

| Asn | Ala | Glu | Ile | Cys | Leu | Leu | Pro | Leu | Asp | Tyr | Gly | Pro | Cys | Arg | Ala |
|---|---|---|---|---|---|---|---|---|---|---|---|---|---|---|---|
| 1 | | | | 5 | | | | | 10 | | | | | 15 | |

| Leu | Leu | Leu | Arg | Tyr | Tyr | Tyr | Asp | Arg | Tyr | Thr | Gln | Ser | Cys | Arg | Gln |
|---|---|---|---|---|---|---|---|---|---|---|---|---|---|---|---|
| | | | 20 | | | | | 25 | | | | | 30 | | |

| Phe | Leu | Tyr | Gly | Gly | Cys | Glu | Gly | Asn | Ala | Asn | Asn | Phe | Tyr | Thr | Trp |
|---|---|---|---|---|---|---|---|---|---|---|---|---|---|---|---|
| | | 35 | | | | | 40 | | | | | 45 | | | |

| Glu | Ala | Cys | Asp | Asp | Ala | Cys | Trp | Arg | Ile |
|---|---|---|---|---|---|---|---|---|---|
| | 50 | | | | | 55 | | | |

(2) INFORMATION FOR SEQ ID NO:40:

(i) SEQUENCE CHARACTERISTICS:
      (A) LENGTH:58 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:40:

```
Asn Ala Glu Ile Cys Leu Leu Pro Leu Asp Gly Gly Pro Cys Arg Ala
 1               5                  10                  15

Ala His Leu Arg Tyr Tyr Tyr Asp Arg Tyr Thr Gln Ser Cys Glu Gln
             20                  25                  30

Phe Ser Tyr Gly Gly Cys Glu Gly Asn Ala Asn Asn Phe Tyr Thr Trp
         35                  40                  45

Glu Ala Cys Asp Asp Ala Cys Trp Arg Ile
         50                  55
```

( 2 ) INFORMATION FOR SEQ ID NO:41:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:41:

```
Val Pro Lys Val Cys Arg Leu Gln Val Ser Val Asp Asp Gln Cys Glu
 1               5                  10                  15

Gly Ser Thr Glu Lys Tyr Phe Phe Asn Leu Ser Ser Met Thr Cys Glu
             20                  25                  30

Lys Phe Phe Ser Gly Gly Cys His Arg Asn Arg Ile Glu Asn Arg Phe
         35                  40                  45

Pro Asp Glu Ala Thr Cys Met Gly Phe Cys Ala Pro Lys
         50                  55                  60
```

( 2 ) INFORMATION FOR SEQ ID NO:42:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:42:

```
Val Pro Lys Val Cys Arg Leu Gln Val Ser Val Asp Asp Gln Cys Arg
 1               5                  10                  15

Ala Ala His Pro Lys Tyr Phe Phe Asn Leu Ser Ser Met Thr Cys Glu
             20                  25                  30

Glu Phe Phe Ser Gly Gly Cys His Arg Asn Arg Ile Glu Asn Arg Phe
         35                  40                  45

Pro Asp Glu Ala Thr Cys Met Gly Phe Cys Ala Pro Lys
         50                  55                  60
```

( 2 ) INFORMATION FOR SEQ ID NO:43:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:43:

```
Ile Pro Ser Phe Cys Tyr Ser Pro Lys Asp Glu Gly Leu Cys Ser Ala
 1               5                  10                  15

Asn Val Thr Arg Tyr Tyr Phe Asn Pro Arg Tyr Arg Thr Cys Asp Ala
```

|           |           |           |           | 20        |           |           |           | 25        |           |           |           | 30        |           |
|-----------|-----------|-----------|-----------|-----------|-----------|-----------|-----------|-----------|-----------|-----------|-----------|-----------|-----------|

Phe Thr Tyr Thr Gly Cys Gly Gly Asn Asp Asn Asn Phe Val Ser Arg
         35                   40                   45

Glu Asp Cys Lys Arg Ala Cys Ala Lys Ala
    50                 55

( 2 ) INFORMATION FOR SEQ ID NO:44:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

Ile Pro Ser Phe Cys Tyr Ser Pro Lys Asp Glu Gly His Cys Arg Ala
 1                 5                   10                 15

Ala His Gln Arg Tyr Tyr Phe Asn Pro Arg Tyr Arg Thr Cys Asp Ala
         20                   25                   30

Phe Thr Tyr Thr Gly Cys Gly Gly Asn Asp Asn Asn Phe Val Ser Arg
         35                   40                   45

Glu Asp Cys Lys Arg Ala Cys Ala Lys Ala
    50                 55

( 2 ) INFORMATION FOR SEQ ID NO:45:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

Lys Glu Asp Ser Cys Gln Leu Gly Tyr Ser Ala Gly Pro Cys Met Gly
 1                 5                   10                 15

Met Thr Ser Arg Tyr Phe Tyr Asn Gly Thr Ser Met Ala Cys Glu Thr
         20                   25                   30

Phe Gln Tyr Gly Gly Cys Met Gly Asn Gly Asn Asn Phe Val Thr Glu
         35                   40                   45

Lys Glu Cys Leu Gln Thr Cys Arg Thr Val
    50                 55

( 2 ) INFORMATION FOR SEQ ID NO:46:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:46:

Lys Glu Asp Ser Cys Gln Leu Gly Tyr Asp Ala Gly Pro Cys Arg Gly
 1                 5                   10                 15

Ala His Pro Arg Tyr Phe Tyr Asn Gly Thr Ser Met Ala Cys Glu Thr
         20                   25                   30

Phe Ser Tyr Gly Gly Cys Gly Gly Asn Gly Asn Asn Phe Val Thr Glu
         35                   40                   45

```
Lys Glu Cys Leu Gln Thr Cys Arg Thr Val
 50                  55
```

( 2 ) INFORMATION FOR SEQ ID NO:47:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:47:

```
Thr Val Ala Ala Cys Asn Leu Pro Ile Val Arg Gly Pro Cys Arg Ala
 1               5                  10                  15
Phe Ile Gln Leu Trp Ala Phe Asp Ala Val Lys Gly Lys Cys Val Leu
                 20                  25                  30
Phe Pro Tyr Gly Gly Cys Gln Gly Asn Gly Asn Lys Phe Tyr Ser Glu
             35                  40                  45
Lys Glu Cys Arg Glu Tyr Cys Gly Val Pro
 50                  55
```

( 2 ) INFORMATION FOR SEQ ID NO:48:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

```
Thr Val Ala Ala Cys Asn Leu Pro Ile Asp Asp Gly Pro Cys Arg Ala
 1               5                  10                  15
Ala His Gln Leu Trp Ala Phe Asp Ala Val Lys Gly Lys Cys Glu Glu
                 20                  25                  30
Phe Ser Tyr Gly Gly Cys Glu Gly Asn Gly Asn Lys Phe Tyr Ser Glu
             35                  40                  45
Lys Glu Cys Arg Glu Tyr Cys Gly Val Pro
 50                  55
```

( 2 ) INFORMATION FOR SEQ ID NO:49:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:49:

```
Thr Val Ala Ala Cys Asn Leu Pro Ile Asp Asp Gly Pro Cys Arg Ala
 1               5                  10                  15
Ala His Gln Arg Trp Ala Phe Asp Ala Val Lys Gly Lys Cys Glu Glu
                 20                  25                  30
Phe Ser Tyr Gly Gly Cys Gln Gly Asn Gly Asn Lys Phe Tyr Ser Glu
             35                  40                  45
Lys Glu Cys Arg Glu Tyr Cys Gly Val Pro
 50                  55
```

( 2 ) INFORMATION FOR SEQ ID NO:50:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:50:

```
Val Arg Glu Val Cys Ser Glu Gln Ala Glu Thr Gly Pro Cys Arg Ala
 1               5                  10                      15

Met Ile Ser Arg Trp Tyr Phe Asp Val Thr Glu Gly Lys Cys Ala Pro
                20                  25                  30

Phe Phe Tyr Gly Gly Cys Gly Gly Asn Arg Asn Asn Phe Asp Thr Glu
            35                  40                  45

Glu Tyr Cys Met Ala Val Cys Gly Ser Ala
     50                  55
```

( 2 ) INFORMATION FOR SEQ ID NO:51:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:51:

```
Val Arg Glu Val Cys Ser Glu Gln Ala Glu Thr Gly Pro Cys Arg Ala
 1               5                  10                      15

Ala His Pro Arg Trp Tyr Phe Asp Val Thr Glu Gly Lys Cys Glu Glu
                20                  25                  30

Phe Ser Tyr Gly Gly Cys Gly Gly Asn Arg Asn Asn Phe Asp Thr Glu
            35                  40                  45

Glu Tyr Cys Met Ala Val Cys Gly Ser Ala
     50                  55
```

( 2 ) INFORMATION FOR SEQ ID NO:52:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:52:

```
Xaa Xaa Xaa Xaa Cys Xaa Xaa Xaa Xaa Xaa Xaa Gly Xaa Cys Xaa Xaa
 1               5                  10                      15

Xaa Xaa Xaa Xaa Xaa Xaa Xaa Xaa Xaa Xaa Xaa Xaa Xaa Cys Xaa Xaa
                20                  25                  30

Phe Xaa Xaa Xaa Gly Cys Xaa Xaa Xaa Xaa Xaa Xaa Xaa Xaa Xaa Xaa
            35                  40                  45

Xaa Xaa Cys Xaa Xaa Xaa Cys Xaa Xaa Xaa
     50                  55
```

( 2 ) INFORMATION FOR SEQ ID NO:53:

( i ) SEQUENCE CHARACTERISTICS:
    ( A ) LENGTH: 58 amino acids
    ( B ) TYPE: amino acid
    ( C ) STRANDEDNESS: single ( D ) TOPOLOGY: linear ( i i ) MOLECULE TYPE: protein ( x i ) SEQUENCE DESCRIPTION: SEQ ID NO:53:

```
Leu Pro Asn Val Cys Ala Phe Pro Met Glu Lys Gly Pro Cys Gln Thr
 1               5                  10                  15
Tyr Met Thr Arg Trp Phe Phe Asn Phe Glu Thr Gly Glu Cys Glu Leu
            20                  25                  30
Phe Ala Tyr Gly Gly Cys Gly Gly Asn Ser Asn Asn Phe Leu Arg Lys
            35                  40                  45
Glu Lys Cys Glu Lys Phe Cys Lys Phe Thr
 50                  55
```

( 2 ) INFORMATION FOR SEQ ID NO:54:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:54:

```
Leu Pro Asn Val Cys Ala Phe Pro Met Glu Asp Gly Pro Cys Arg Ala
 1               5                  10                  15
Ala His Pro Arg Trp Phe Phe Asn Phe Glu Thr Gly Glu Cys Glu Glu
            20                  25                  30
Phe Ala Tyr Gly Gly Cys Gly Gly Asn Ser Asn Asn Phe Leu Arg Lys
            35                  40                  45
Glu Lys Cys Glu Lys Phe Cys Lys Phe Thr
 50                  55
```

( 2 ) INFORMATION FOR SEQ ID NO:55:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

```
Arg Pro Asp Phe Cys Leu Glu Pro Pro Glu Thr Gly Pro Cys Arg Ala
 1               5                  10                  15
Ala His Pro Arg Tyr Phe Tyr Asn Ala Lys Ala Gly Leu Cys Glu Glu
            20                  25                  30
Phe Val Tyr Gly Gly Cys Gly Ala Lys Arg Asn Asn Phe Lys Ser Ala
            35                  40                  45
Glu Asp Cys Met Arg Thr Cys Gly Gly Ala
 50                  55
```

( 2 ) INFORMATION FOR SEQ ID NO:56:

( i ) SEQUENCE CHARACTERISTICS:
        ( A ) LENGTH:186 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:56:

| | | | | |
|---|---|---|---|---|
| GCCGAGATGC | ATTCCTTCTG | CGCCTTCAAG | GCTGATGATG | GTCNTTGTAA | 50 |
| AGSTNNTNNS | NNGCGTTTCT | TCTTCAACAT | CTTCACGCGT | CAGTGCSAGS | 100 |
| AATTCNNSTA | CGGTGGTTGT | NNSGGTAACC | AGAACCGGTT | CGAATCTCTA | 150 |
| GAGGAATGTA | AGAAGATGTG | CACTCGTGAC | GGCGCC | | 186 |

( 2 ) INFORMATION FOR SEQ ID NO:57:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:57:

| Ala | Glu | Met | His | Ser | Phe | Cys | Ala | Phe | Lys | Ala | Asp | Asp | Gly | Xaa | Cys |
|---|---|---|---|---|---|---|---|---|---|---|---|---|---|---|---|
| 1 | | | | 5 | | | | | 10 | | | | | 15 | |
| Lys | Xaa | Xaa | Xaa | Xaa | Arg | Phe | Phe | Phe | Asn | Ile | Phe | Thr | Arg | Gln | Cys |
| | | | 20 | | | | | 25 | | | | | 30 | | |
| Xaa | Xaa | Phe | Xaa | Tyr | Gly | Gly | Cys | Xaa | Gly | Asn | Gln | Asn | Arg | Phe | Glu |
| | | 35 | | | | | 40 | | | | | 45 | | | |
| Ser | Leu | Glu | Glu | Cys | Lys | Lys | Met | Cys | Thr | Arg | Asp | Gly | Ala | | |
| | 50 | | | | | 55 | | | | | 60 | | | | |

( 2 ) INFORMATION FOR SEQ ID NO:58:

( i ) SEQUENCE CHARACTERISTICS:
        ( A ) LENGTH:4 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:58:

Lys Arg Pro Arg
1

( 2 ) INFORMATION FOR SEQ ID NO:59:

( i ) SEQUENCE CHARACTERISTICS:
        ( A ) LENGTH:13 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:59:

AAAAGGCCTC GAG         13

( 2 ) INFORMATION FOR SEQ ID NO:60:

( i ) SEQUENCE CHARACTERISTICS:
        ( A ) LENGTH:14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:60:

```
Lys  Arg  Glu  Ala  Ala  Glu  Pro  Trp  Gly  Ala  Xaa  Xaa  Leu  Glu
 1              5                    10
```

( 2 ) INFORMATION FOR SEQ ID NO:61:

( i ) SEQUENCE CHARACTERISTICS:
      ( A ) LENGTH:42 bases
      ( B ) TYPE: nucleic acid
      ( C ) STRANDEDNESS: single
      ( D ) TOPOLOGY: linear ( i i ) MOLECULE TYPE:other nucleic acid
      ( A ) DESCRIPTION:synthetic DNA fragment ( x i ) SEQUENCE DESCRIPTION: SEQ ID NO:61:

```
AAAAGGGAAG  CGGCCGAGCC  ATGGGGCGCC  TAATAGCTCG  AG                    42
```

( 2 ) INFORMATION FOR SEQ ID NO:62:

( i ) SEQUENCE CHARACTERISTICS:
      ( A ) LENGTH:66 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:62:

```
Lys  Arg  Glu  Ala  Ala  Glu  Met  His  Ser  Phe  Cys  Ala  Phe  Lys  Ala  Asp
 1              5                    10                       15

Asp  Gly  Pro  Cys  Lys  Ala  Ile  Met  Lys  Arg  Phe  Phe  Phe  Asn  Ile  Phe
              20                    25                       30

Thr  Arg  Gln  Cys  Glu  Glu  Phe  Ile  Tyr  Gly  Gly  Cys  Glu  Gly  Asn  Gln
          35                    40                   45

Asn  Arg  Phe  Glu  Ser  Leu  Glu  Glu  Cys  Lys  Lys  Met  Cys  Thr  Arg  Asp
     50                    55                        60

Gly  Ala
 65
```

( 2 ) INFORMATION FOR SEQ ID NO:63:

( i ) SEQUENCE CHARACTERISTICS:
      ( A ) LENGTH:210 bases
      ( B ) TYPE: nucleic acid
      ( C ) STRANDEDNESS: single
      ( D ) TOPOLOGY: linear ( i i ) MOLECULE TYPE:other nucleic acid
      ( A ) DESCRIPTION:synthetic DNA fragment ( x i ) SEQUENCE DESCRIPTION: SEQ ID NO:63:

```
AAAAGGGAAG  CGGCCGAGAT  GCATTCCTTC  TGCGCTTTCA  AAGCTGATGA        50

CGGTCCGTGT  AAAGCTATCA  TGAAACGTTT  CTTCTTCAAC  ATTTTCACGC       100

GTCAGTGCGA  GGAATTCATT  TACGGTGGTT  GTGAAGGTAA  CCAGAACCGG       150

TTCGAATCTC  TAGAGGAATG  TAAGAAGATG  TGCACTCGTG  ACGGCGCCTA       200

ATAGCTCGAG                                                        210
```

( 2 ) INFORMATION FOR SEQ ID NO:64:

( i ) SEQUENCE CHARACTERISTICS:
      ( A ) LENGTH:58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:64:

| Met | His | Ser | Phe | Cys | Ala | Phe | Lys | Ala | Asp | Asp | Gly | His | Cys | Ala | Ala |
|---|---|---|---|---|---|---|---|---|---|---|---|---|---|---|---|
| 1 | | | | 5 | | | | | 10 | | | | | 15 | |
| Asn | His | Gln | Arg | Phe | Phe | Phe | Asn | Ile | Phe | Thr | Arg | Gln | Cys | Glu | Glu |
| | | | 20 | | | | | 25 | | | | | 30 | | |
| Phe | Ser | Tyr | Gly | Gly | Cys | Gly | Gly | Asn | Gln | Asn | Arg | Phe | Glu | Ser | Leu |
| | | 35 | | | | | 40 | | | | | 45 | | | |
| Glu | Glu | Cys | Lys | Lys | Met | Cys | Thr | Arg | Asp | | | | | | |
| 50 | | | | | | 55 | | | | | | | | | |

( 2 ) INFORMATION FOR SEQ ID NO:65:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

| Met | His | Ser | Phe | Cys | Ala | Phe | Lys | Ala | Asp | Gly | Gly | Arg | Cys | Ala | Gly |
|---|---|---|---|---|---|---|---|---|---|---|---|---|---|---|---|
| 1 | | | | 5 | | | | | 10 | | | | | 15 | |
| Ala | His | Pro | Arg | Trp | Phe | Phe | Asn | Ile | Phe | Thr | Arg | Gln | Cys | Glu | Glu |
| | | | 20 | | | | | 25 | | | | | 30 | | |
| Phe | Ser | Tyr | Gly | Gly | Cys | Gly | Gly | Asn | Gln | Asn | Arg | Phe | Glu | Ser | Leu |
| | | 35 | | | | | 40 | | | | | 45 | | | |
| Glu | Glu | Cys | Lys | Lys | Met | Cys | Thr | Arg | Asp | | | | | | |
| 50 | | | | | | 55 | | | | | | | | | |

( 2 ) INFORMATION FOR SEQ ID NO:66:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:66:

| Met | His | Ser | Phe | Cys | Ala | Phe | Lys | Ala | Asp | Asp | Gly | Pro | Cys | Ser | Ala |
|---|---|---|---|---|---|---|---|---|---|---|---|---|---|---|---|
| 1 | | | | 5 | | | | | 10 | | | | | 15 | |
| Ala | His | Pro | Arg | Trp | Phe | Phe | Asn | Ile | Phe | Thr | Arg | Gln | Cys | Glu | Glu |
| | | | 20 | | | | | 25 | | | | | 30 | | |
| Phe | Ser | Tyr | Gly | Gly | Cys | Gly | Gly | Asn | Gln | Asn | Arg | Phe | Glu | Ser | Leu |
| | | 35 | | | | | 40 | | | | | 45 | | | |
| Glu | Glu | Cys | Lys | Lys | Met | Cys | Thr | Arg | Asp | | | | | | |
| 50 | | | | | | 55 | | | | | | | | | |

( 2 ) INFORMATION FOR SEQ ID NO:67:

( i ) SEQUENCE CHARACTERISTICS:
        ( A ) LENGTH:97 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:67:

```
CCTCCTATGC  ATTCCTTCTG  CGCCTTCAAG  GCTRASRNTG  GTNNTTGTAR           50

AGSTRNTCNS  CNSCGTTKST  TCTTAACAT   CTTCACGCGT  TCCCTCC              97
```

( 2 ) INFORMATION FOR SEQ ID NO:68:

( i ) SEQUENCE CHARACTERISTICS:
        ( A ) LENGTH:23 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:68:

```
GGAGGGAACG  CGTGAAGATG  TTG                                          23
```

( 2 ) INFORMATION FOR SEQ ID NO:69:

( i ) SEQUENCE CHARACTERISTICS:
        ( A ) LENGTH:28 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:69:

```
Met  His  Ser  Phe  Cys  Ala  Phe  Lys  Ala  Xaa  Xaa  Gly  Xaa  Cys  Xaa  Xaa
 1              5                         10                          15

Xaa  Xaa  Xaa  Arg  Xaa  Phe  Phe  Asn  Ile  Phe  Thr  Arg
               20                        25
```

( 2 ) INFORMATION FOR SEQ ID NO:70:

( i ) SEQUENCE CHARACTERISTICS:
        ( A ) LENGTH:4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

```
Glu  Ala  Ala  Glu
 1              4
```